US010912600B2

(12) United States Patent
Kitagawa et al.

(10) Patent No.: US 10,912,600 B2
(45) Date of Patent: Feb. 9, 2021

(54) HIGH-FREQUENCY ELECTROSURGICAL TREATMENT INSTRUMENT FOR OPERATIONS AND HIGH-FREQUENCY ELECTROSURGICAL SYSTEM FOR OPERATIONS

(71) Applicants: KEIO UNIVERSITY, Tokyo (JP); OLYMPUS CORPORATION, Tokyo (JP)

(72) Inventors: Yuko Kitagawa, Tokyo (JP); Minoru Tanabe, Tokyo (JP); Norihiro Yamada, Hino (JP)

(73) Assignees: KEIO UNIVERSITY, Tokyo (JP); OLYMPUS CORPORATION, Tokyo (JP)

( * ) Notice: Subject to any disclaimer, the term of this patent is extended or adjusted under 35 U.S.C. 154(b) by 266 days.

(21) Appl. No.: 14/339,009

(22) Filed: Jul. 23, 2014

(65) Prior Publication Data

US 2014/0350540 A1     Nov. 27, 2014

Related U.S. Application Data

(63) Continuation of application No. PCT/JP2013/083650, filed on Dec. 16, 2013.
(Continued)

(51) Int. Cl.
*A61B 18/14* (2006.01)
*A61B 18/12* (2006.01)
*A61B 18/00* (2006.01)

(52) U.S. Cl.
CPC ...... *A61B 18/1445* (2013.01); *A61B 18/1206* (2013.01); *A61B 2018/00589* (2013.01); *A61B 2018/126* (2013.01); *A61B 2218/002* (2013.01)

(58) Field of Classification Search
CPC ............ A61B 18/1442; A61B 18/1445; A61B 18/1447; A61B 18/1206; A61B 2018/1206
See application file for complete search history.

(56) References Cited

U.S. PATENT DOCUMENTS 4,567,890 A    2/1986  Ohta et al.
5,456,684 A *  10/1995 Schmidt ................. A61B 17/29
                                                    604/35
(Continued)

FOREIGN PATENT DOCUMENTS

EP      2 591 734 A1    5/2013
JP      A-07-047083     2/1995
(Continued)

OTHER PUBLICATIONS

Jan. 14, 2014 International Search Report issued in International Application No. PCT/JP2013/083650 (with partial translation).
(Continued)

*Primary Examiner* — Michael F Peffley
*Assistant Examiner* — Bo Ouyang
(74) *Attorney, Agent, or Firm* — Oliff PLC

(57) ABSTRACT

A high-frequency electrosurgical treatment instrument for operations, includes a pair of forceps pieces, an insulating member, a transmission member, a manipulation rod member, a distal end cover member, a shaft member and a manipulation portion. The instrument, includes a flow channel portion formed between the manipulation rod member and the shaft member, the flow channel portion being disposed along a longitudinal direction of the manipulation rod member to allow liquid to flow; a groove portion that communicates with the flow channel portion to allow the liquid to flow from the flow channel portion; and an opening portion that communicates with the groove portion to supply (Continued)

the liquid near the proximal end portions of the pair of forceps pieces.

22 Claims, 19 Drawing Sheets

Related U.S. Application Data

(60) Provisional application No. 61/750,942, filed on Jan. 10, 2013.

(56) References Cited

U.S. PATENT DOCUMENTS

| | | | | |
|---|---|---|---|---|
| 5,891,142 | A * | 4/1999 | Eggers | A61B 18/1442 |
| | | | | 606/51 |
| 6,953,461 | B2 * | 10/2005 | McClurken | A61B 18/14 |
| | | | | 606/206 |
| 8,540,711 | B2 * | 9/2013 | Dycus | A61B 18/1445 |
| | | | | 606/45 |
| 9,113,903 | B2 * | 8/2015 | Unger | A61B 18/1445 |
| 2005/0033278 | A1 * | 2/2005 | McClurken | A61B 18/14 |
| | | | | 606/41 |
| 2008/0119846 | A1 * | 5/2008 | Rioux | A61B 18/1477 |
| | | | | 606/41 |
| 2010/0069903 | A1 * | 3/2010 | Allen, IV | A61B 17/2816 |
| | | | | 606/45 |
| 2010/0185196 | A1 | 7/2010 | Sakao et al. | |
| 2010/0185197 | A1 * | 7/2010 | Sakao | A61B 18/085 |
| | | | | 606/51 |

FOREIGN PATENT DOCUMENTS

| | | |
|---|---|---|
| JP | A-2004-275548 | 10/2004 |
| JP | A-2005-502424 | 1/2005 |
| JP | A-2005-224426 | 8/2005 |
| JP | A-2007-020969 | 2/2007 |
| JP | A-2011-218182 | 11/2011 |
| WO | WO 2012/124653 A1 | 9/2012 |

OTHER PUBLICATIONS

Aug. 8, 2016 Extended Search Report issued in European Patent Application No. 13870674.2.

Oct. 18, 2016 Office Action issued in Chinese Patent Application No. 201380011809.8.

* cited by examiner

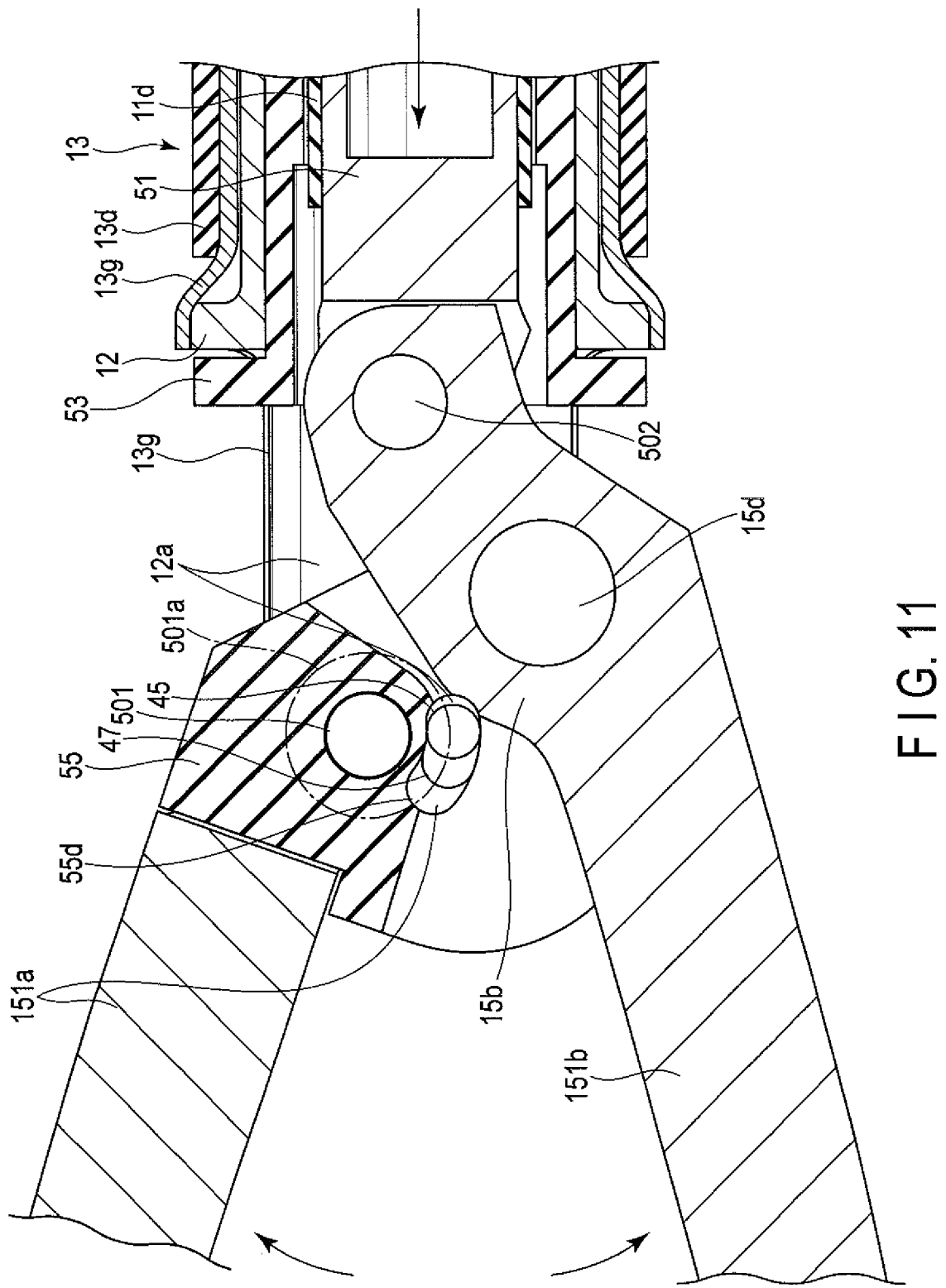
F I G. 11

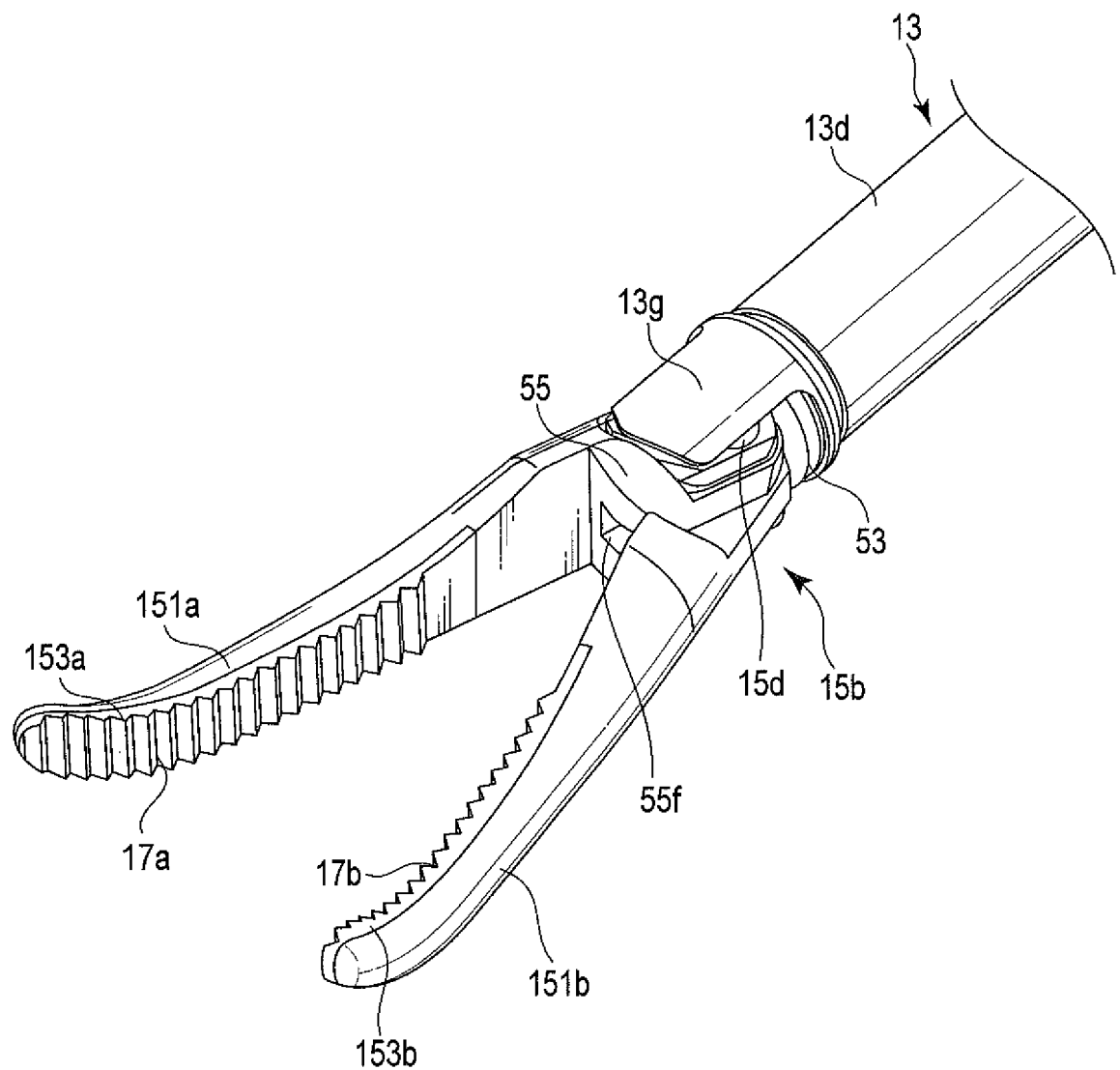
F I G. 16

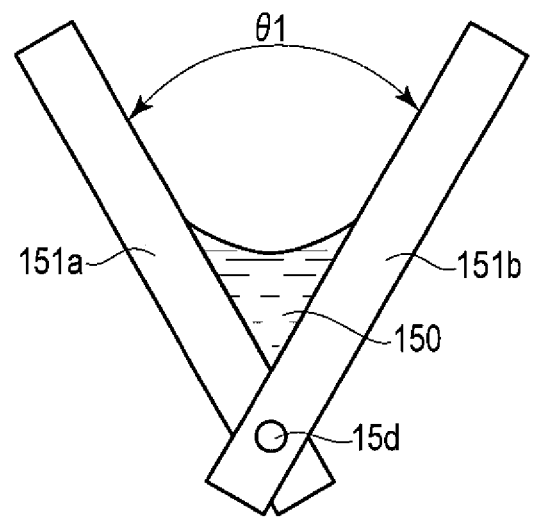
F I G. 17A
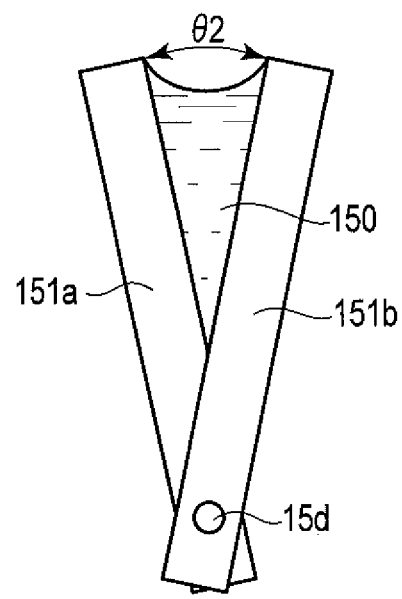
F I G. 17B

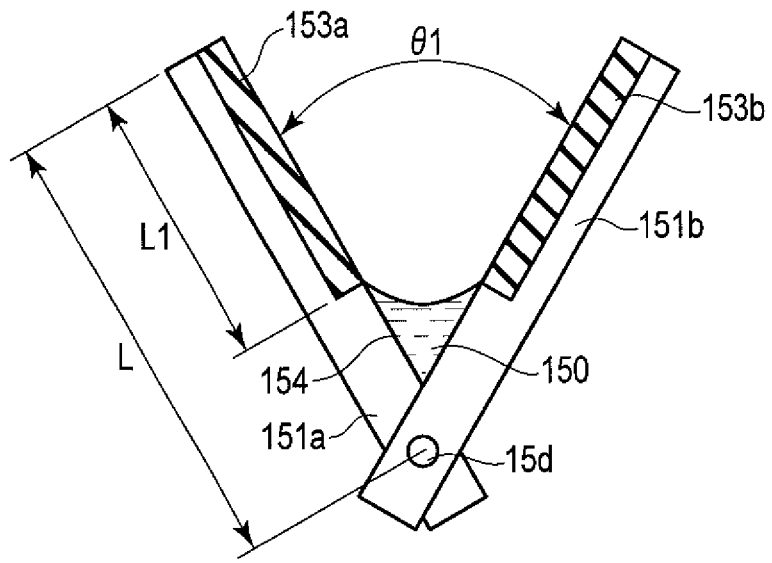
F I G. 17C
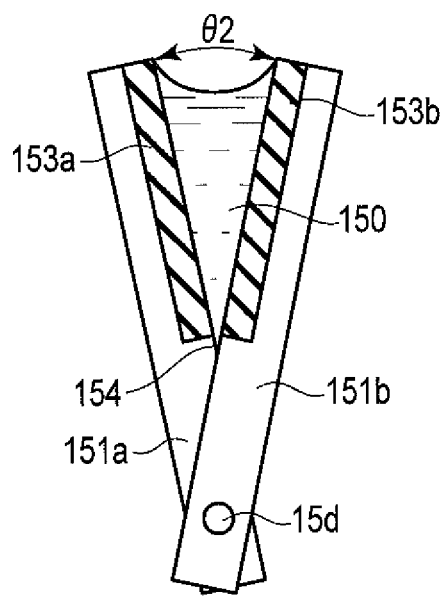
F I G. 17D

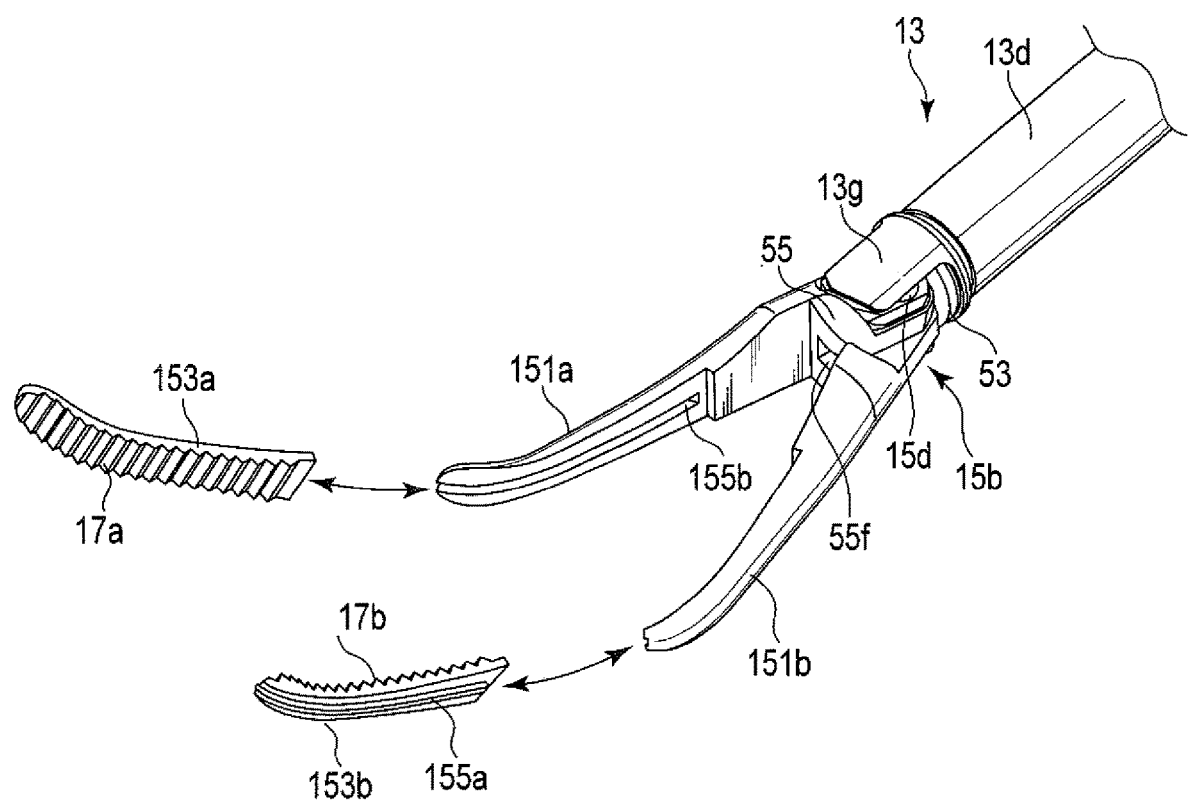
F I G. 18

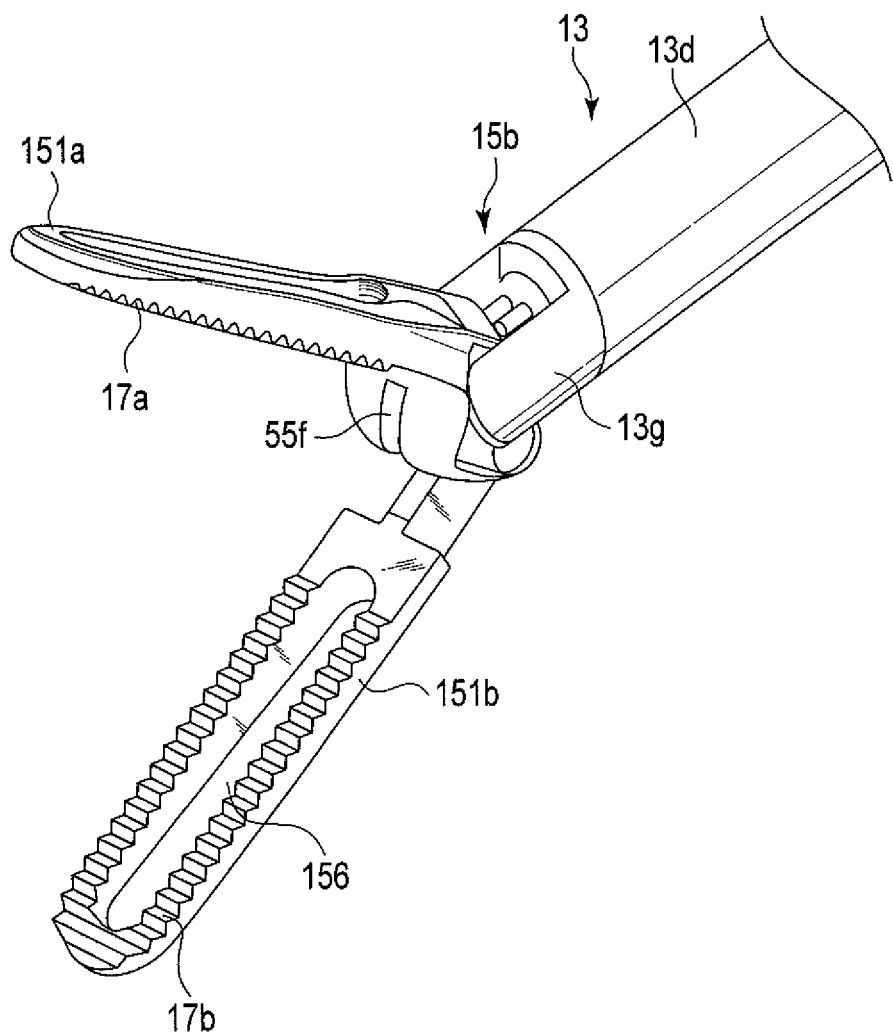
F I G. 19

HIGH-FREQUENCY ELECTROSURGICAL TREATMENT INSTRUMENT FOR OPERATIONS AND HIGH-FREQUENCY ELECTROSURGICAL SYSTEM FOR OPERATIONS

CROSS-REFERENCE TO RELATED APPLICATIONS

This application is a Continuation Application of PCT Application No. PCT/JP2013/083650, filed Dec. 16, 2013 and based upon and claiming the benefit of U.S. Provisional Application No. 61/750,942, filed Jan. 10, 2013, the entire contents of all of which are incorporated herein by reference.

BACKGROUND OF THE INVENTION

1. Field of the Invention

The present invention relates to a high-frequency electrosurgical treatment instrument for operations and a high-frequency electrosurgical system for operations, in which liquid is conveyed to an affected area.

2. Description of the Related Art

In general surgical operations and endoscopic treatment, affected areas often bleed. To stop the bleeding, electrocoagulation with supply of a liquid is effective.

Jpn. PCT National Publication No. 2005-502424, for example, discloses operation equipment for treating tissue. This operation equipment is a monopolar high-frequency electrical treatment instrument for the abdominal cavity, and is capable of coagulation by high-frequency power while supplying liquid to an affected area.

U.S. Pat. No. 4,567,890, for example, discloses a high-frequency forceps for laparotomy. This high-frequency forceps is bipolar.

Jpn. Pat. Appln. KOKAI Publication No. 2004-275548, for example, discloses a beak-shaped treatment instrument for an endoscope, which treats an affected area as a source of bleeding immediately after washing off the blood and other substances.

Jpn. Pat. Appln. KOKAI Publication No. 2007-20969, for example, discloses a high-frequency treatment instrument for an endoscope, in which a nozzle pipe and a water conveyance tube are not disconnected from each other even when the water conveyance operation is performed with the nozzle pipe closed.

Jpn. Pat. Appln. KOKAI Publication No. 2005-224426, for example, discloses a treatment instrument for an endoscope, which is capable of identifying a bleeding site quickly and reliably and providing necessary treatment promptly and reliably.

BRIEF SUMMARY OF THE INVENTION

An aspect of a high-frequency electrosurgical treatment instrument for operations of the present invention includes a pair of forceps pieces including grip surfaces opposed to each other to grip an affected area, the forceps pieces being capable of being opened and closed relative to each other; an insulating member disposed at proximal end portions of the forceps pieces and insulates one of the forceps pieces from the other forceps piece; a transmission member coupled to one of the forceps pieces such that one of the forceps pieces and the other forceps pieces are pivotably coupled to each other; a manipulation rod member including a distal end portion and a proximal end portion, the distal end portion being fixed to the transmission member; a distal end cover member including a fulcrum that pivotably couples one of the pair of forceps pieces; a shaft member into which the manipulation rod member is inserted to cover the manipulation rod member so as to wrap the manipulation rod member from the distal end portion to the proximal end portion, the shaft member being inserted into a body cavity together with the manipulation rod member; a manipulation portion including a movable handle removably coupled to the proximal end portion of the manipulation rod member and a fixed handle removably coupled to a proximal end of the shaft member; a flow channel portion formed between the manipulation rod member and the shaft member in a radial direction of the shaft member, the flow channel portion being disposed along a longitudinal direction of the manipulation rod member, when the manipulation rod member is inserted into the shaft member, to allow liquid to flow; a groove portion that communicates with the flow channel portion and is disposed along the longitudinal direction of the manipulation rod member on an outer peripheral surface of the distal end cover member to allow the liquid to flow from the flow channel portion; and an opening portion that communicates with the groove portion to supply the liquid near the proximal end portions of the pair of forceps pieces.

An aspect of a high-frequency electrosurgical system for operations of the present invention includes a pair of forceps pieces including grip surfaces opposed to each other to grip an affected area, the forceps pieces being capable of being opened and closed relative to each other; an insulating member disposed at proximal end portions of the forceps pieces and insulates one of the forceps pieces from the other forceps piece; a transmission member coupled to one of the forceps pieces such that one of the forceps pieces and the other forceps pieces are pivotably coupled to each other; a manipulation rod member including a distal end portion and a proximal end portion, the distal end portion being fixed to the transmission member; a distal end cover member including a fulcrum that pivotably couples with one of the forceps pieces; a shaft member into which the manipulation rod member is inserted to cover the manipulation rod member so as to wrap the manipulation rod member from the distal end portion to the proximal end portion, the shaft member being inserted into a body cavity together with the manipulation rod member; a manipulation portion including a movable handle removably coupled to the proximal end portion of the manipulation rod member and a fixed handle removably coupled to a proximal end portion of the shaft member; a flow channel portion formed between the manipulation rod member and the shaft member in a radial direction of the shaft member, the flow channel portion being disposed along a longitudinal direction of the manipulation rod member, when the manipulation rod member is inserted into the shaft member, to allow liquid to flow; a groove portion that communicates with the flow channel portion and is disposed along the longitudinal direction of the manipulation rod member on an outer peripheral surface of the distal end cover member to allow the liquid to flow from the flow channel portion; an opening portion that communicates with the groove portion to supply the liquid near the proximal end portions of the pair of forceps pieces; a connector including a return electrode that electrically conducts with one of the forceps pieces and an active electrode that electrically conducts with the other forceps piece; a liquid conveyance unit that conveys the liquid toward the flow channel portion; and a power supply electrically connected with the connector to supply power to the forceps pieces.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 11 is a diagram showing a communicative state of the through hole portions with the forceps pieces opened.

FIG. 16 is a perspective view of the vicinity of a distal end portion of a shaft member with insulating grip members disposed according to a second modification.

FIG. 17A is a diagram showing a relationship between an opening angle between forceps pieces and a wet area of the forceps pieces wet with a liquid.

FIG. 17B is a diagram showing a relationship between an opening angle between forceps pieces and a wet area of the forceps pieces wet with a liquid.

FIG. 17C is a diagram showing a relationship between an opening angle between forceps pieces and a wet area of the forceps pieces wet with a liquid.

FIG. 17D is a diagram showing a relationship between an opening angle between forceps pieces and a wet area of the forceps pieces wet with a liquid.

FIG. 18 is a perspective view of the vicinity of a distal end portion of a shaft member, with removable insulating grip members.

FIG. 19 is a perspective view of the vicinity of a distal end portion of a forceps unit with an open window portion disposed in a grip surface according to a third modification.

DETAILED DESCRIPTION OF THE INVENTION

Embodiments of the present invention will be described in detail below with reference to the drawings.

First Embodiment

[Configuration]

Referring to FIG. 1, FIG. 2, FIG. 3, FIG. 4, FIG. 5, FIG. 6, FIG. 7, and FIG. 8, a first embodiment will be described. In some of the drawings, some members are not shown for clarification of the drawings.

Figure 1:
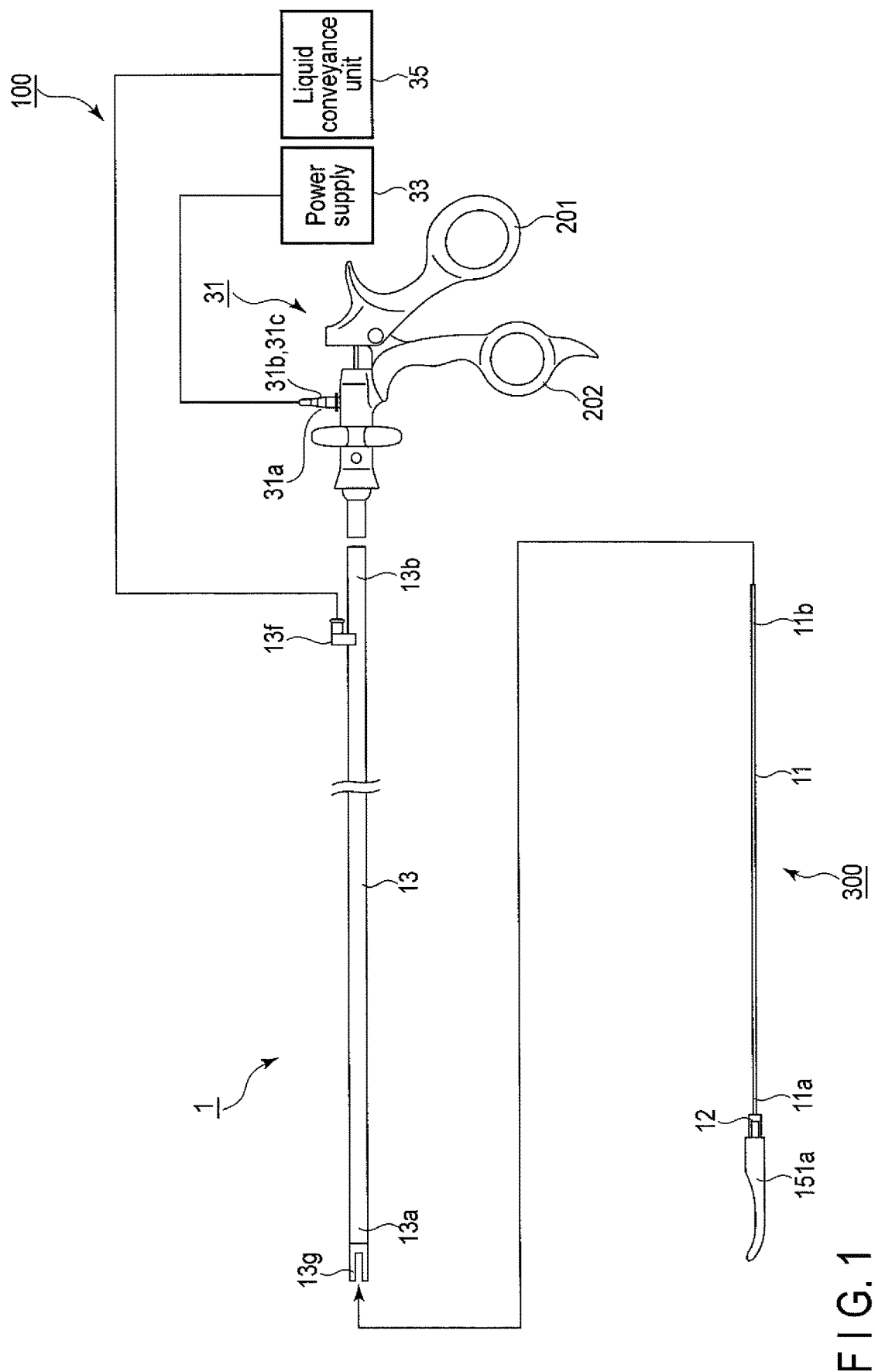
FIG. 1 is a schematic diagram of a treatment system in a first embodiment according to the present invention.

As shown in FIG. 1, a treatment system 100 comprises a treatment instrument 1, a power supply 33, and a liquid conveyance unit 35.

The treatment instrument 1 as shown in FIG. 1 is, for example, a bipolar electrical treatment instrument for use in surgical operations, which is a high-frequency electrosurgical treatment instrument for operations. Examples of the surgical operations (the applications of the treatment instrument 1) mainly include liver resection, kidney resection, and pancreas resection under a laparoscope. In the surgical operations as described above, the treatment instrument 1 is used, for example, for stripping, gripping, resection, and sampling of living tissue, and electrocoagulation and astriction for bleeding. In the main applications, that is, in resection of parenchymal organs such as the liver, kidneys, and pancreas, oozing bleeding is likely to occur, in which the resented surface bleeds uniformly. Electrocoagulation with supply of liquid is effective for such bleeding. This allows the bleeding resected surface to be coagulated uniformly. Moreover, excessive coagulation is prevented and heat damage to living tissue is minimized because the living tissue is heated to temperatures not higher than the boiling point of the liquid.

Figure 2:
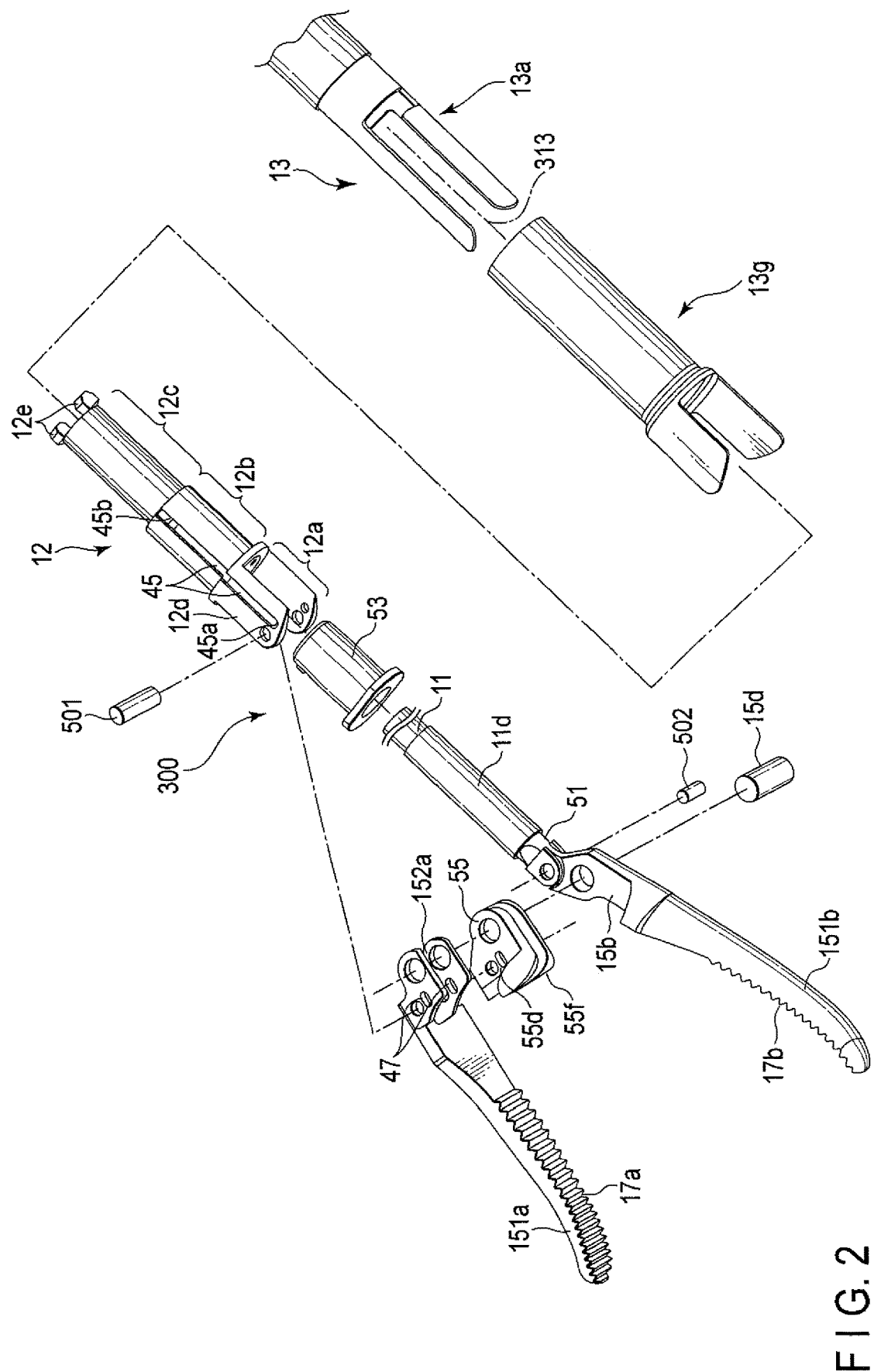
FIG. 2 is an exploded perspective view of the vicinity of a distal end portion of a shaft member.

As shown in FIG. 1 and FIG. 2, the treatment instrument 1 comprises a forceps unit 300 including a pair of forceps pieces 151a, 151b and a manipulation rod member 11, and a shaft member 13 into which the manipulation rod member 11 is inserted so that the shaft member 13 covers (externally covers) the manipulation rod member 11 so as to wrap the manipulation rod member 11 from a distal end portion 11a of the manipulation rod member 11 to a proximal end portion 11b of the manipulation rod member 11 and is inserted into the body cavity together with the manipulation rod member 11. The treatment instrument 1 further comprises a manipulation portion 31 including a movable handle 201 removably coupled to the proximal end portion 11b of the manipulation rod member 11 and a fixed handle 202 removably coupled to a proximal end portion 13b of the shaft member 13, the movable handle 201 is opened/closed relative to the fixed handle 202 thereby opening/closing the forceps pieces 151a, 151b.

As shown in FIG. 1 and FIG. 2, the forceps unit 300 includes the pair of forceps pieces 151a, 151b, an insulating member 55, a transmission member 51, the elongated manipulation rod member 11 having a sheath member 11d, an insulating tubular member 53, a distal end cover member 12, a fulcrum pin member 501, an action pin member 15d, and an action pin member 502.

The pair of forceps pieces 151a, 151b have grip surfaces 17a, 17b opposed to each other to grip an affected area. The forceps pieces 151a, 151b are capable of being opened/closed relative to each other. The grip surfaces 17a, 17b have projections and depressions so as to facilitate gripping of an affected area. The forceps pieces 151a, 151b are a pair of bipolar electrodes.

The insulating member 55 is disposed at the proximal end portions of the forceps pieces 151a, 151b and insulates one forceps piece 151a from the other forceps piece 151b. The insulating member 55 is fitted in a proximal end opening portion 152a provided at the proximal end portion of the forceps piece 151a. The insulating member 55 is pivotably coupled together with the forceps piece 151a to a proximal end portion 15b of the forceps piece 151b via the action pin member 15d. That is, the action pin member 15d couples the insulating member 55, the forceps piece 151a, and the forceps piece 151b together. The insulating member 55 has an opening portion 55f. The proximal end portion of the opening portion 55f is fitted in part of the proximal end portion 15b of the forceps piece 151b.

The transmission member 51 couples with one of the forceps piece 151a and the forceps piece 151b such that the forceps piece 151a and the forceps piece 151b are pivotably coupled with each other. The transmission member 51 is coupled with the proximal end portion 15b of the forceps piece 151b, for example, via the action pin member 502.

Figure 8:
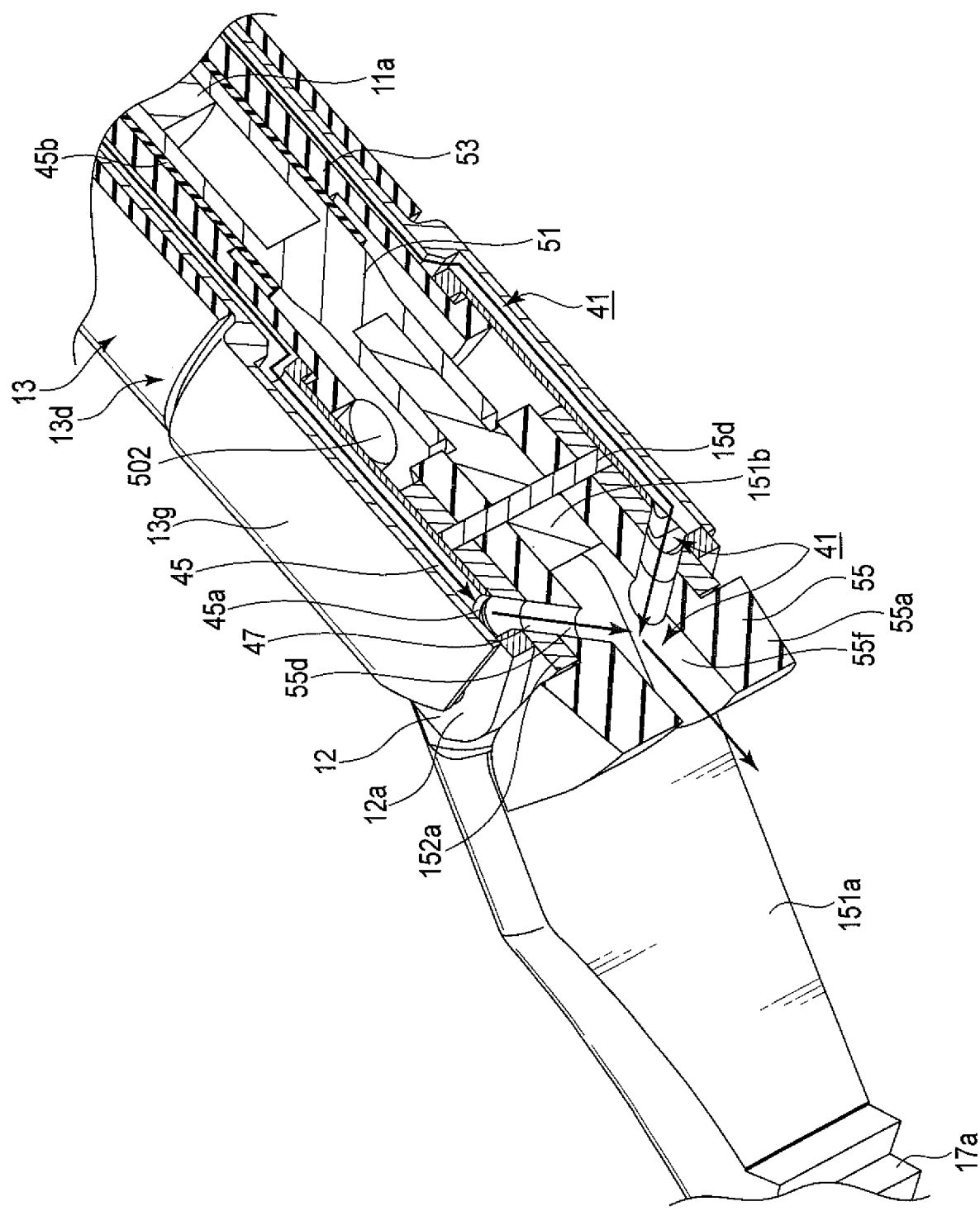
FIG. 8 is a diagram showing a channel through which liquid flows in the vicinity of an insulating member.
Figure 9:
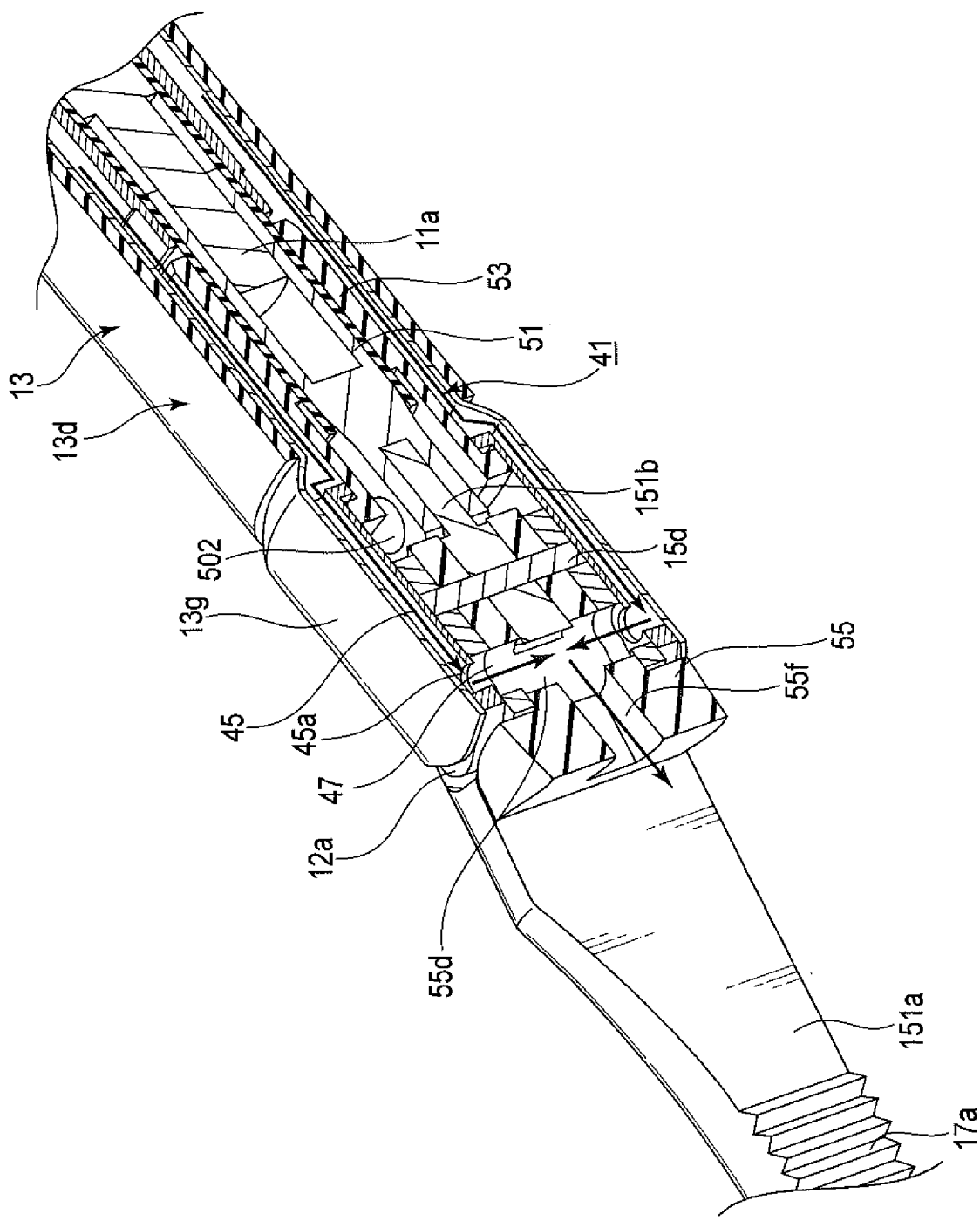
FIG. 9 is a diagram showing a channel through which liquid flows in the vicinity of an insulating member in a second embodiment.

As shown in FIG. 1, the manipulation rod member 11 has the distal end portion 11a and the proximal end portion 11b. As shown in FIG. 8 and FIG. 9, the distal end portion 11a is fixed to the transmission member 51. The transmission member 51 and the manipulation rod member 11 are fixed by screw fastening, brazing, thermal fitting, or any other means.

Figure 3:
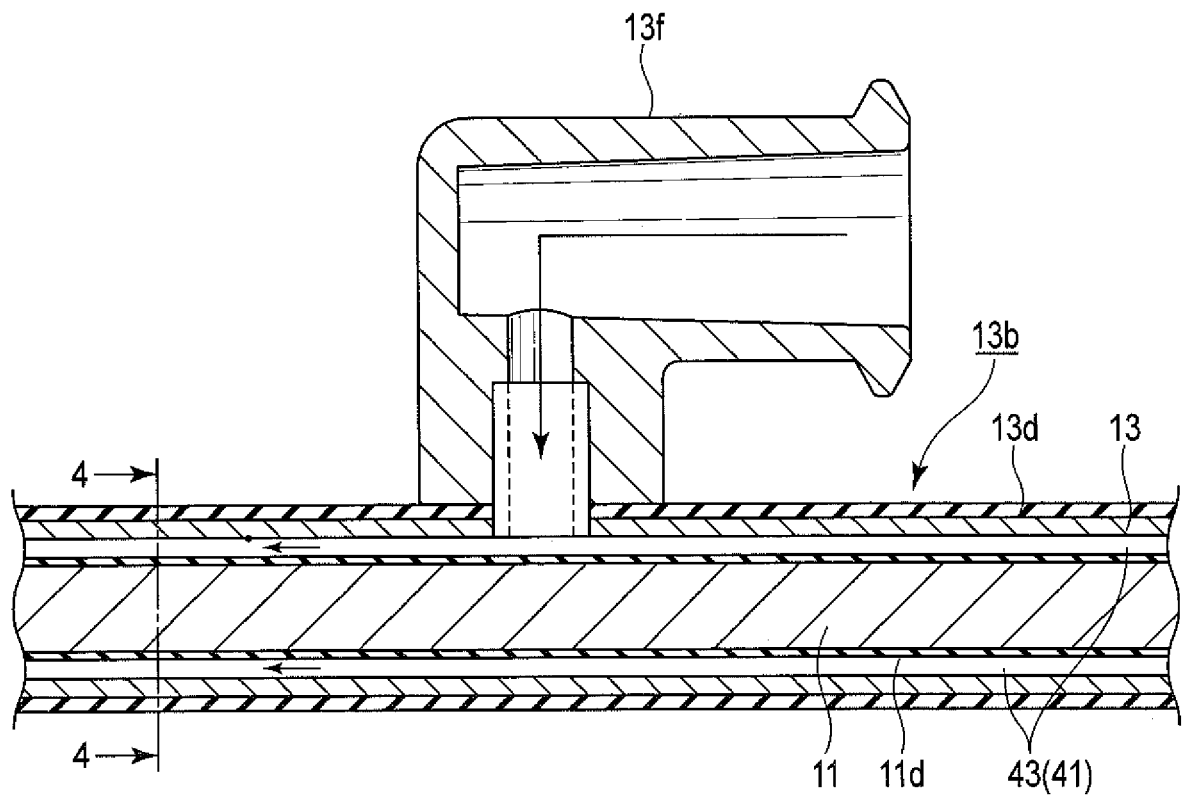
FIG. 3 is a diagram showing the internal structure of a manipulation rod member and the shaft member in the vicinity of an inlet port portion.
Figure 4:
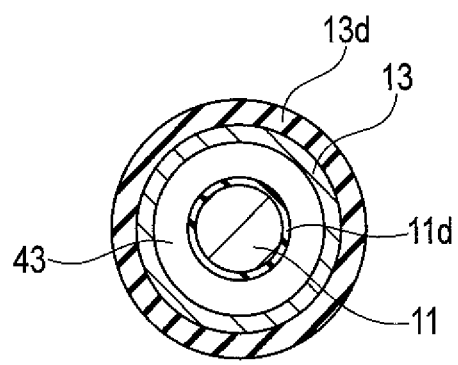
FIG. 4 is a cross-sectional view along a line 4-4 in FIG. 3.

The manipulation rod member 11 is, for example, a metal cylindrical member. As shown in FIG. 3 and FIG. 4, the manipulation rod member 11 has the sheath member 11d that sheathes the manipulation rod member 11. The sheath member 11d is an insulating member that insulates the manipulation rod member 11. Such a sheath member 11d functions as an insulating coating such as PTFE.

As shown in FIG. 2, the distal end cover member 12 has a bifurcated distal end portion 12a, a large diameter portion 12b having the shape of a hollow cylinder, and a small diameter portion 12c. The small diameter portion 12c is disposed at the proximal end portion of the distal end cover member 12. The large diameter portion 12b is sandwiched between the distal end portion 12a and the small diameter portion 12c in the axial direction of the distal end cover member 12. The distal end portion 12a is integral with the large diameter portion 12b, and the large diameter portion 12b is integral with the small diameter portion 12c.

The small diameter portion 12c has projection portions 12e disposed at the proximal end portion of the small diameter portion 12c. The projection portions 12e are removably engaged with engagement cuts 313 of the shaft member 13 described later, whereby the shaft member 13 and the distal end cover member 12 are removably fixed.

The distal end portion 12a accommodates the proximal end opening portion 152a of the forceps piece 151a, the insulating member 55, and the proximal end portion 15b of the forceps piece 151b. The distal end portion 12a has the fulcrum pin member 501 that functions as the fulcrum of pivot. The distal end portion 12a is coupled with the forceps piece 151a and the insulating member 55 via the fulcrum pin member 501, for example, such that the forceps piece 151a and the insulating member 55 pivot relative to the distal end portion 12a with the fulcrum pin member 501 as a fulcrum.

As described above, the distal end cover member 12 has the fulcrum pin member 501 that functions as a fulcrum for pivotably coupling, for example, the forceps piece 151a to the distal end portion 12a.

The insulating tubular member 53 having the shape of a hollow cylinder is fixed in the interior of the large diameter portion 12b of the distal end cover member 12. In other words, the large diameter portion 12b can accommodate the insulating tubular member 53, and the accommodating large diameter portion 12b can be removably fixed to the insulating tubular member 53. The fixing is thermal fitting or adhesion, or both. The inner diameter of the insulating tubular member 53 and the inner diameter of the small diameter portion 12c have such a size that allows insertion and removal of the transmission member 51 and the manipulation rod member 11.

As shown in FIG. 3 and FIG. 4, the shaft member 13 has a cylindrical shape such that the manipulation rod member 11 is inserted into the shaft member 13 and that the shaft member 13 covers the manipulation rod member 11. Here, as shown in FIG. 3 and FIG. 4, the inner diameter of the shaft member 13 is larger than the outer diameter of the manipulation rod member 11 including the sheath member 11d. Accordingly, when the manipulation rod member 11 is inserted into the shaft member 13, a flow channel portion 43 functioning as a space portion is formed between the manipulation rod member 11 and the shaft member 13 in the radial direction of the shaft member 13. This flow channel portion 43 represents the space portion between the exterior of the manipulation rod member 11 and the interior of the shaft member 13, in other words, between the outer peripheral surface of the manipulation rod member 11 (the sheath member 11d) and the inner peripheral surface of the shaft member 13. The flow channel portion 43 is also covered with the shaft member 13. As shown in FIG. 3, the flow channel portion 43 is disposed along the longitudinal direction of the shaft member 13 (the manipulation rod member 11). Such a flow channel portion 43 is included in a flow channel portion (liquid conveyance portion) 41 through which liquid flows, for example, from the proximal end portion 11b side toward the distal end portion 11a side of the manipulation rod member 11 by means of the liquid conveyance unit 35. In the flow channel portion 43, liquid flows from the proximal end portion side toward the distal end portion side of the flow channel portion 43.

As described above, the flow channel portion 43 is formed between the manipulation rod member 11 and the shaft member 13 in the radial direction of the shaft member 13 and is disposed along the longitudinal direction of the manipulation rod member 11 when the manipulation rod member 11 is inserted into the shaft member 13. In the flow channel portion 43, liquid flows from the proximal end portion side of the flow channel portion 43 toward the distal end portion side of the flow channel portion 43.

The shaft member 13 contains, for example, a metal such as SUS. Such a shaft member 13 has a sheath member 13d that sheathes the shaft member 13, as shown in FIG. 3 and FIG. 4. The sheath member 13d has an insulating material that insulates the shaft member 13. Such a sheath member 13d has an insulating coating such as PTFE.

As shown in FIG. 1 and FIG. 3, the shaft member 13 has an inlet port portion 13f that is disposed on the proximal end portion 13b side of the shaft member 13 and through which liquid from the liquid conveyance unit 35 outside the treatment instrument 1 is fed to the flow channel portion 43.

The inlet port portion 13*f* is a supply port that is coupled with the liquid conveyance unit 35 and through which liquid from the liquid conveyance unit 35 is supplied to the flow channel portion 43. The inlet port portion 13*f* passes through the shaft member 13 and the sheath member 13*d* and communicates with the flow channel portion 43 (the interior of the shaft member 13). The liquid supplied from the liquid conveyance unit 35 flows into the flow channel portion 43 through the inlet port portion 13*f* and is conveyed through from the flow channel portion 43 toward the distal end cover member 12.

Figure 5:
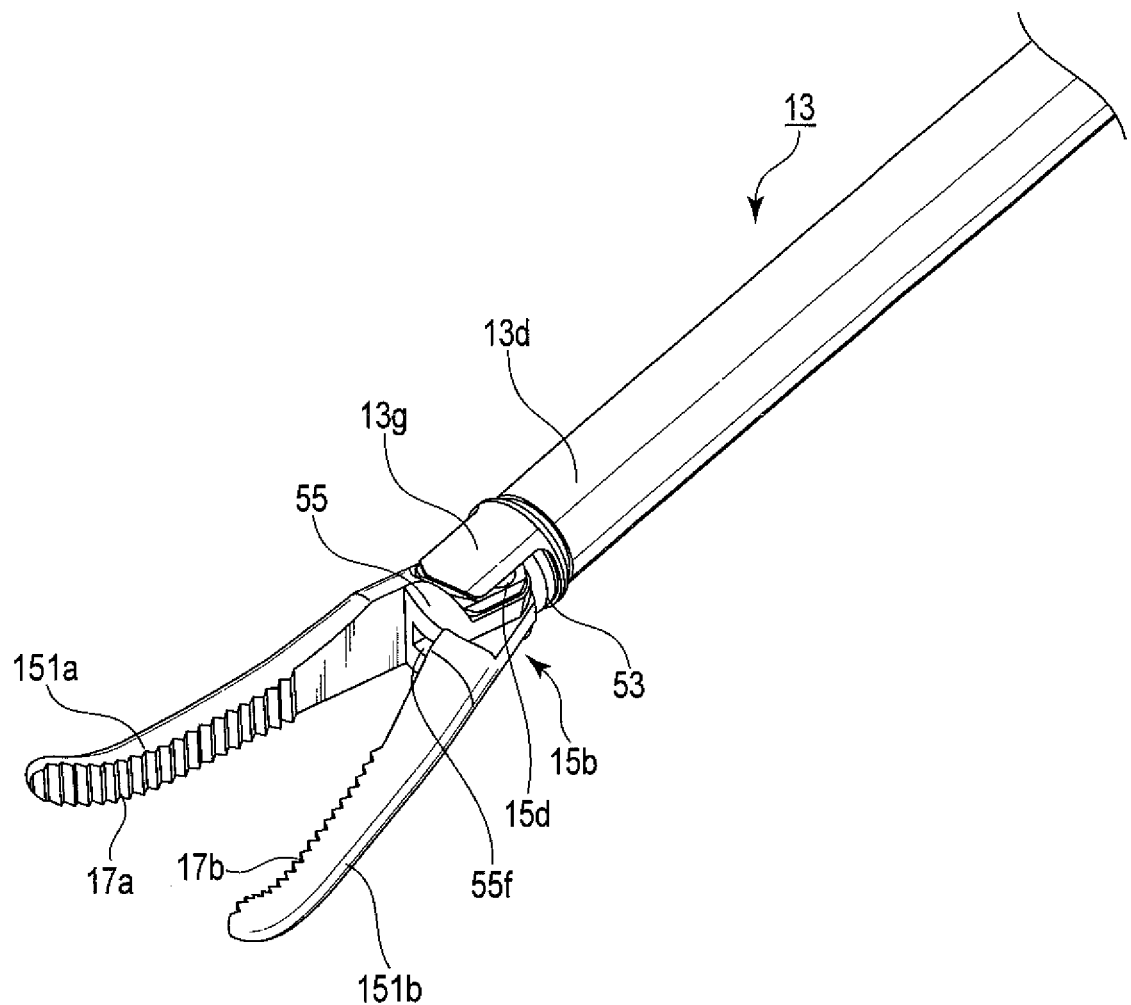
FIG. 5 is a perspective view of the vicinity of the distal end portion of the shaft member.
Figure 6:
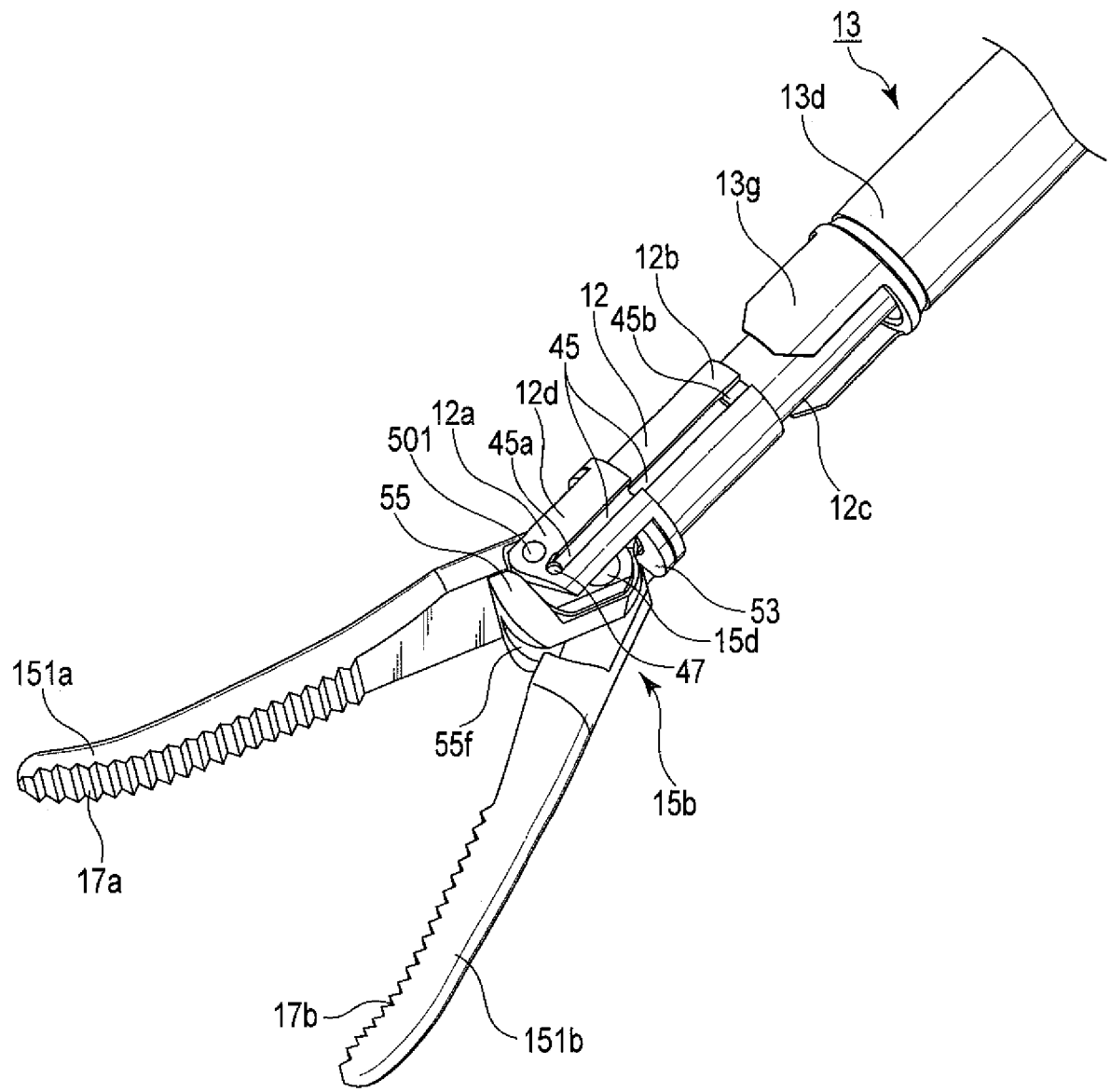
FIG. 6 shows a state in which the manipulation rod member is taken out of the shaft member in a state shown in FIG. 5.

As shown in FIG. 5 and FIG. 6, the shaft member 13 has a groove cover member 13*g* that covers groove portions 45 described later so as to cap the groove portions 45 when the manipulation rod member 11 is inserted into the shaft member 13. The groove cover member 13*g* is formed as a cylindrical member into which a distal end portion 13*a* of the shaft member 13 and the distal end cover member 12 are inserted. As described above, the groove cover member 13*g* is disposed at the distal end portion 13*a* side of the shaft member 13. Such a groove cover member 13*g* is included in the shaft member 13. The distal end portion of the groove cover member 13*g* is exposed, and the proximal end portion of the groove cover member 13*g* is covered by the sheath member 13*d*. When the distal end portion 13*a* of the shaft member 13 and the distal end cover member 12 are inserted into the groove cover member 13*g*, the proximal end portion of the groove cover member 13*g* covers the engagement cuts 313 and proximal end portions 45*b* of the groove portions 45. The distal end portion of the groove cover member 13*g* is bifurcated into two. The distal end portions of the groove cover member 13*g* are disposed so as to correspond to the arrangement position of distal end portions 45*a* of the groove portions 45. The distal end portions of the groove cover member 13*g* are therefore disposed 180° apart from each other in the circumferential direction in the longitudinal direction of the shaft member 13 (the manipulation rod member 11). When the distal end cover member 12 is inserted into the groove cover member 13*g*, the distal end portions of the groove cover member 13*g* cover the distal end portions 45*a* of the groove portions 45. The groove cover member 13*g* may be separated from the distal end portion 13*a* as mentioned above or may be integral with the distal end portion 13*a*. In the case where the groove cover member 13*g* is integral with the distal end portion 13*a*, the groove cover member 13*g* is part of the bifurcated distal end portion 13*a*.

Figure 7:
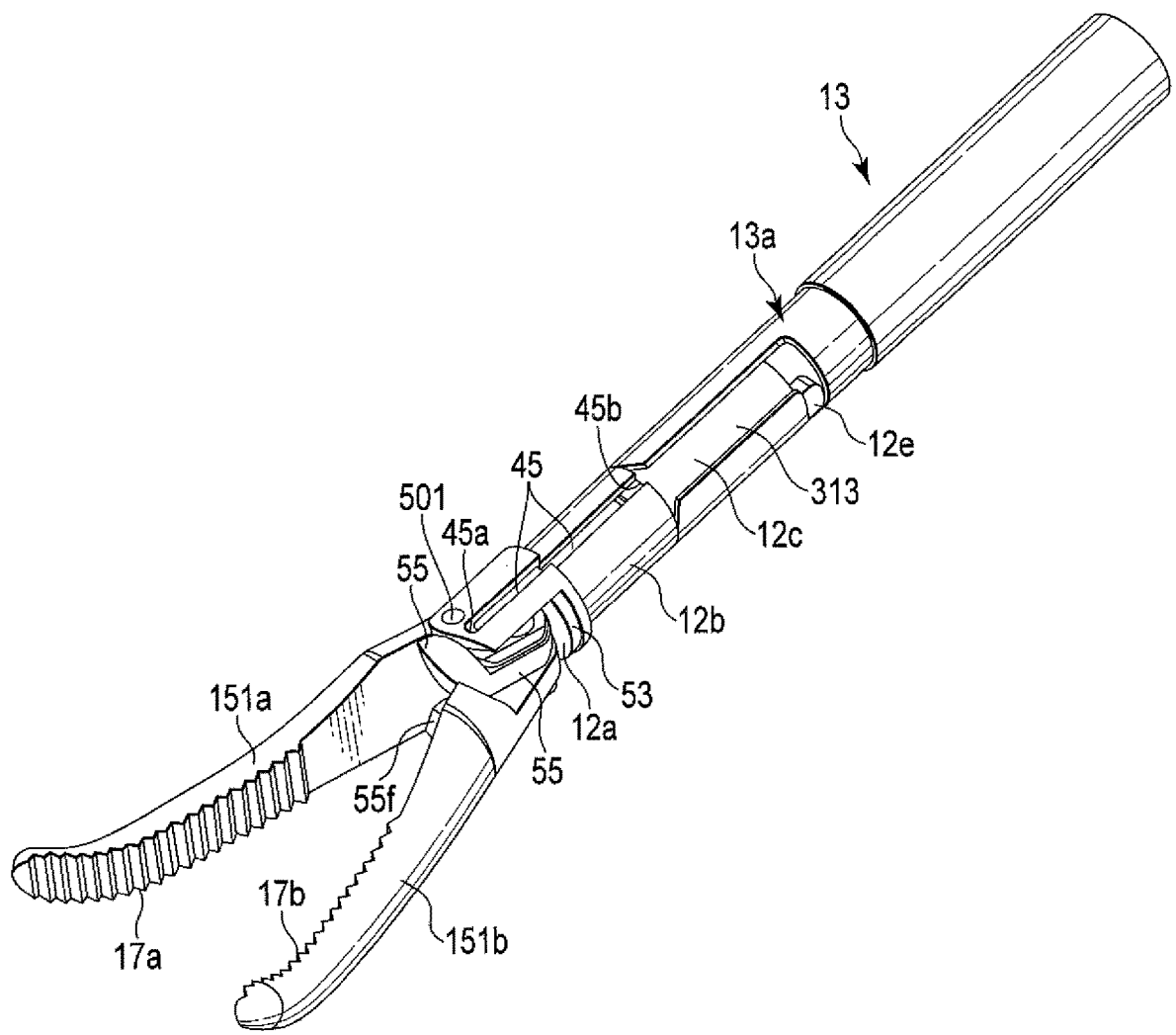
FIG. 7 is a diagram showing an engagement and fixing part between a distal end cover member and the shaft member, without showing a sheath member and a groove cover member.

As shown in FIG. 2, the shaft member 13 has two engagement cuts 313 substantially in the shape of a L that are disposed at the distal end portion 13*a* of the shaft member 13. The engagement cuts 313 are provided axially symmetric with each other. FIG. 7 shows the distal end portion of the treatment instrument 1 without showing the sheath member 13*d* and the groove cover member 13*g*. As shown in FIG. 7, the projection portions 12*e* enter the engagement cuts 313, and the projection portions 12*e* are engaged with the proximal end portions of the engagement cuts 313, whereby the distal end cover member 12 is fixed to the shaft member 13. The shaft member 13 including the engagement cuts 313 contains a metal such as SUS as described above. Accordingly, the shaft member 13 is engaged with the distal end cover member 12 of a metal such as SUS so that electrical continuity is established between the shaft member 13 and the distal end cover member 12.

As shown in FIG. 1, when the manipulation rod member 11 is inserted into (put into) the shaft member 13 from the proximal end portion 11*b* of the manipulation rod member 11 toward the distal end portion 13*a* of the shaft member 13, the proximal end portion 11*b* of the manipulation rod member 11 is fixed to the movable handle 201. The shaft member 13 is thereby fixed to the fixed handle 202. Here, since the projection portions 12*e* are engaged with the engagement cuts 313, the distal end cover member 12 is fixed to the fixed handle 202 via the shaft member 13, and the manipulation rod member 11 and the transmission member 51 are fixed to the movable handle 201. When the movable handle 201 is closed relative to the fixed handle 202, the manipulation rod member 11 is pulled toward the manipulation portion 31, and the forceps pieces 151*a*, 151*b* are closed. Conversely, when the movable handle is opened relative to the fixed handle, the manipulation rod member 11 is pushed toward the forceps pieces 151*a*, 151*b*, and the forceps pieces 151*a*, 151*b* are opened.

The treatment instrument 1 in the present embodiment is a bipolar high-frequency electrical treatment instrument. The forceps pieces 151*a*, 151*b*, the distal end cover member 12, the manipulation rod member 11, the transmission member 51, and the shaft member 13 including the engagement cuts 313 contain a metal such as SUS. The insulating tubular member 53 fitted on the inner surface of the large diameter portion 12*b*, the sheath member 11*d* that sheathes the manipulation rod member 11 and the transmission member 51, the insulating member 55, the action pin member 15*d*, and the action pin member 502 are formed of, for example, an insulating material such as PFA, PTFE, alumina, aluminium nitride, or zirconia.

As shown in FIG. 1, the manipulation portion 31 has a connector portion 31*a* to be connected to the power supply 33. The connector portion 31*a* has an active electrode 31*b* and a return electrode 31*c*. The active electrode 31*b* is in electrical conduction with the manipulation rod member 11, the transmission member 51, and the forceps piece 151*b*. The return electrode 31*c* is in electrical conduction with the shaft member 13, the distal end cover member 12, and the forceps piece 151*a*. The conducting path of the active electrode 31*b* from the manipulation rod member 11 to the forceps piece 151*b* through the transmission member 51 and the conducting path of the return electrode 31*c* from the forceps piece 151*a* to the shaft member 13 through the distal end cover member 12 are electrically insulated by the sheath member 11*d*, the insulating tubular member 53, the insulating member 55, the action pin member 15*d*, and the action pin member 502. When high-frequency power is supplied from the power supply 33 to the forceps pieces 151*a*, 151*b* with both of the forceps piece 151*a* and the forceps piece 151*b* in contact with living tissue, liquid, and other substances, a high-frequency current flows from the forceps piece 151*b* toward the living tissue, and a high-frequency current flows from a medium such as the liquid toward the forceps piece 151*a*. The living tissue and the medium such as the liquid are heated by Joule heating because their electrical conductivity is lower than the electrical conductivity of the metal that is the material of the conducting path of the forceps pieces 151*a*, 151*b* to the active electrode 31*b* and the return electrode 31*c*.

The power supply 33 is electrically connected with the connector portion 31*a* to supply power to the forceps pieces 151*a*, 151*b*.

As shown in FIG. 1, the liquid conveyance unit 35 is coupled to the inlet port portion 13*f* to convey liquid from the inlet port portion 13*f* to the flow channel portion 43 and supply the liquid from the opening portion 55*f* of the insulating member 55 toward an affected area. An example of the liquid in the liquid conveyance unit 35 is an isotonic solution having the same osmotic pressure as living tissue in human bodies. An example of the isotonic solution is physiological saline solution.

[Flow Channel Portion 41]

Referring now to FIG. 6 and FIG. 8, the flow channel portion 41 in the present embodiment which conveys liquid from the inlet port portion 13*f* toward the opening portion 55*f* provided in the insulating member 55 of the forceps pieces 151*a*, 151*b* will be described.

The flow channel portion 41 includes the inlet port portion 13*f* described above, the flow channel portion 43 described above, the engagement cuts 313 of the shaft member 13, the groove portions 45 in communication with the engagement cuts 313 at the proximal end portions 45*b* of the groove portions 45, through hole portions 47 in communication with the groove portions 45, through hole portions 55*d* in communication with the through hole portions 47, and the opening portion 55*f* described above in communication with the through hole portions 55*d*.

As shown in FIG. 3, the flow channel portion 43 is formed between the manipulation rod member 11 and the shaft member 13 in the radial direction and is disposed along the longitudinal direction of the shaft member 13 (the manipulation rod member 11).

The groove portion 45 communicates with the flow channel portion 43 and is disposed along the longitudinal direction of the manipulation rod member 11 on an outer peripheral surface 12*d* of the distal end cover member 12. Liquid flows into the groove portion 45 from the flow channel portion 43. The groove portions 45 are disposed at both of the two bifurcated distal end portions 12*a* of the distal end cover member 12.

As shown in FIG. 2, the groove portion 45 is disposed from the through hole portion 47 provided at the bifurcated distal end portion 12*a* of the distal end cover member 12 to the large diameter portion 12*b*, along the longitudinal direction of the shaft member 13 (the manipulation rod member 11). The distal end portion 45*a* of the groove portion 45 is formed in such a manner that the distal end cover member 12 is partially depressed. The distal end portion 45*a* functions as the flow channel portion 41. The proximal end portion 45*b* of the groove portion 45 is disposed at the large diameter portion 12*b* so as to pass through the large diameter portion 12 in the thickness direction of the large diameter portion 12. That is, the proximal end portion 45*b* functions as a through hole portion. As shown in FIG. 8, the outer peripheral surface of the insulating tubular member 53 inserted into the large diameter portion 12*b* functions as the bottom surface of the proximal end portion 45*b*. The proximal end portion 45*b* and the outer peripheral surface of the insulating tubular member 53 function as the flow channel portion 41. Such two groove portions 45 are disposed symmetrically with respect to the center axis of the manipulation rod member 11. The groove portion 45 is disposed, for example, orthogonally to the forceps pieces 151*a*, 151*b*. The groove portion 45 is therefore disposed, for example, orthogonally to the opening/closing direction of the forceps pieces 151*a*, 151*b*. As shown in FIG. 7, when the distal end cover member 12 and the shaft member 13 are engaged with and fixed to each other, the opening direction of the groove portion 45 on the proximal end portion 45*b* side generally agrees with the opening direction of the engagement cut 313 of the shaft member 13. As shown in FIG. 5, the groove portion 45 is covered (capped) with the groove cover member 13*g*.

As shown in FIG. 8, the distal end portion 45*a* of the groove portion 45 communicates with the through hole portion 47. The through hole portion 47 is disposed at the proximal end portion of the forceps piece 151*a* so as to pass through the proximal end portion of the forceps piece 151*a*. The liquid flows into the through hole portion 47 from the groove portion 45. The through hole portion 47 communicates with the proximal end opening portion 152*a*. The through hole portion 47 is inclined relative to the longitudinal direction of the shaft member 13 (the manipulation rod member 11). In more detail, the through hole portion 47 passes through the proximal end portion 15*b* at an inclination so as to extend from the outer peripheral surface 12*d* of the distal end cover member 12 toward the center axis of the manipulation rod member 11, that is, so as to be disposed from the exterior to the interior of the manipulation rod member 11. In other words, the forceps piece 151*a* has the through hole portion 47 that is disposed at the proximal end portion of the forceps piece 151*a*, communicates with the distal end portion 45*a* of the groove portion 45, and is inclined relative to the longitudinal direction of the shaft member 13 (the manipulation rod member 11) so as to extend from the outer peripheral surface 12*d* of the distal end cover member 12 toward the center axis of the manipulation rod member 11.

As shown in FIG. 8, the through hole portion 47 communicates with the through hole portion 55*d* that is disposed in the insulating member 55 and communicates with the opening portion 55*f*. The liquid flows into the through hole portion 55*d* from the groove portion 45 through the through hole portion 47. The through hole portion 55*d* is inclined in the same manner as the through hole portion 47.

The opening portion 55*f* is disposed at a distal end portion 55*a* of the insulating member 55. The opening portion 55*f* communicates with the through hole portion 55*d* and is disposed in the insulating member 55 along the longitudinal direction of the insulating member 55. The liquid flows into the opening portion 55*f* from the through hole portion 55*d*. The opening portion 55*f* then supplies the liquid near the proximal end portions of the forceps pieces 151*a*, 151*b*.

As described above, the insulating member 55 has the through hole portion 55*d* that communicates with the through hole portion 47 and is inclined in the same manner as the through hole portion 47, and the opening portion 55*f* that communicates with the through hole portion 55*d* and is disposed along the longitudinal direction of the insulating member 55.

[Operation]

The operating method of the present embodiment will now be described.

As shown in FIG. 1, the manipulation rod member 11 is inserted into (put into) the shaft member 13 so that the flow channel portion 43 is formed as shown in FIG. 3 and FIG. 4. Here, as shown in FIG. 5, the groove cover member 13*g* covers the groove portion 45. As shown in FIG. 1, the manipulation portion 31 is coupled to the proximal end portion 11*b* of the manipulation rod member 11 and the proximal end portion 13*b* of the shaft member 13. The treatment instrument 1 is then inserted into the body cavity.

As shown in FIG. 1, the inlet port portion 13*f* is coupled with the liquid conveyance unit 35. Liquid thus flows from the liquid conveyance unit 35 to the flow channel portion 43 through the inlet port portion 13*f*. The liquid flowing into the flow channel portion 43 flows into the groove portion formed with the engagement cut 313 of the shaft member 13 and the small diameter portion 12*c* of the distal end cover member 12. As shown in FIG. 8, the liquid then flows from the engagement cut 313 in this groove portion into the opening portion 55*f* through the groove portion 45, the through hole portion 47, and the through hole portion 55d. The liquid further flows out of the opening portion 55f toward an affected area.

Since the flow channel portion 43 is covered with the shaft member 13 and the groove portion 45 is covered with the groove cover member 13g, the liquid flows into the opening portion 551 from the inlet port portion 13f without leaking to the outside of the treatment instrument 1.

The forceps pieces 151a, 151b come into contact with the affected area where blood oozes, for example, the resected surface of the liver parenchyma, and the liquid flows onto the resected surface from the opening portion 55f. High-frequency power is then supplied from the power supply 33 to the forceps pieces 151a, 151b. The liquid flowing out of the opening portion 55f near the forceps pieces 151a, 151b is boiled by high-frequency power to coagulate the affected area and stop the bleeding. The affected area is not excessively heated because the boiling point of the liquid such as physiological saline solution is about 100° C. In addition, the treatment instrument 1 stops bleeding efficiently and widely when compared with a treatment instrument that treats an affected area only by high-frequency power without using a liquid, because the affected area soaked in the boiled liquid is coagulated uniformly. Since the treatment instrument 1 is bipolar, heat damage to the affected area in the depth direction is not as large as that of the monopolar type, and the affected area is treated easily and more gently.

In a case where bleeding comes from a particular site, the liquid flows out of the opening portion 55f and washes the affected area, thereby allowing identification of the bleeding point. The movable handle 201 of the manipulation portion 31 is thereafter closed, so that the forceps pieces 151a, 151b pinch tissue near the bleeding point. The forceps pieces 151a, 151b are supplied with high-frequency power from the power supply 33 to coagulate tissue by high-frequency power while pressing the tissue near the bleeding point. In a case where blood spurts from part of the affected area where blood oozes, the forceps pieces 151a, 151b provide high-frequency energy to the bleeding point supplied with the liquid from the opening portion 55f, while pinching and pressing the bleeding point where blood spurts from. The oozing bleeding and the spurting bleeding are thus stopped simultaneously.

Advantageous Effects

As described above, in the present embodiment, the treatment instrument 1 is a bipolar high-frequency electrical treatment instrument which can reduce an invasion and can treat an affected area easily and gently.

In the present embodiment, liquid can be conveyed to an affected area through the flow channel portion 43, the groove portion 45, the through hole portions 47, 55d, and the opening portion 55f. In the present embodiment, the forceps pieces 151a, 151b are high-frequency energized in this state, whereby the affected area can be thermally coagulated with the boiled liquid, and bleeding in a wide range can be stopped quickly and efficiently while preventing excessive heat damage to the affected area. In the present embodiment, the liquid fills up between the forceps pieces 151a, 151b and living tissue in the affected area, thereby preventing adhesion of the living tissue to the forceps pieces 151a, 151b. As described above, in the present embodiment, the affected area can be treated easily by conveying liquid to the affected area.

In the present embodiment, the forceps pieces 151a, 151b can be opened/closed through manipulation of the manipulation portion 31 to allow stripping, gripping, resection, and sampling of living tissue as well as pressing of the bleeding point.

In the present embodiment, the flow channel portion 43 and the groove portion 45 are formed. The flow channel portion 43 and the groove portion 45 are formed as part of the flow channel portion 41 that conveys a liquid, thereby eliminating the need for disposing a tubular member such as a tube serving as the flow channel portion 41 in the interior of the shaft member 13. Accordingly, in the present embodiment, the diameter of the shaft member 13 can be reduced.

In the present embodiment, the flow channel portion 43 is covered with the shaft member 13, and the groove portion 45 is covered with the groove cover member 13g, thereby preventing liquid from leaking to the outside of the treatment instrument 1. The liquid thus can be fed from the inlet port portion 13f to the opening portion 55f without leakage.

In the present embodiment, the inlet port portion 13f enables a clean liquid to constantly flow toward the affected area.

In the present embodiment, two sets of the groove portion 45 and the through hole portions 47, 55d are provided symmetrically with respect to the center axis of the manipulation rod member 11 to allow liquid to be conveyed stably to the affected area without depending on the orientation of the forceps pieces 151a, 151b.

Second Embodiment

Figure 10:
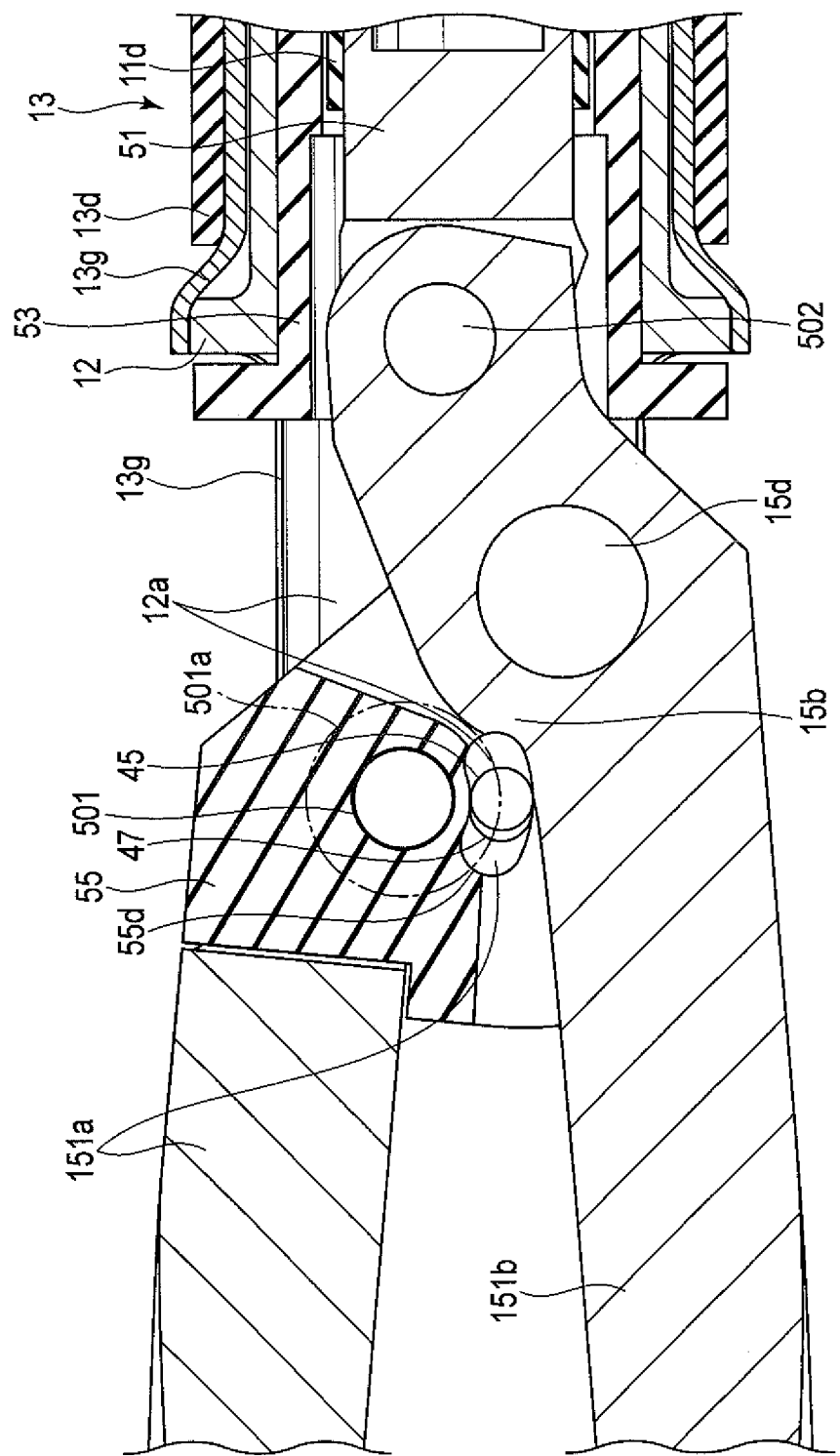
FIG. 10 is a diagram showing a communicative state of through hole portions with forceps pieces closed.

Referring now to FIG. 9, FIG. 10, and FIG. 11, a second embodiment will be described. The same parts as in the foregoing first embodiment are denoted with the same reference signs and a detailed description thereof will be omitted. Some parts are omitted in the drawings for the sake of simplification.

As shown in FIG. 10 and FIG. 11, through hole portions 47, 55d in the present embodiment have the shape of a long hole portion so as to always communicate with a groove portion 45 without being affected by the opening/closing of forceps pieces 151a, 151b. The through hole portions 47, 55d are arranged with the same width on a circumferential line 501a around a fulcrum pin member 501.

In this manner, even when the through hole portion 47 partially overlaps a proximal end portion 15b of the forceps piece 151b due to the opening/closing of the forceps pieces 151a, 151b, the groove portion 45 and the through hole portions 47, 55d are always in communication, and a breakage in communication is prevented. As described above, the communication between the groove portion 45 and the through hole portions 47, 55d is always maintained.

Accordingly, in the present embodiment, the through hole portions 47, 55d can always be opened without being affected by the open/closed angle of the forceps pieces 151a, 151b, so that liquid can easily flow from the groove portion 45 toward the through hole portions 47, 55d.

Third Embodiment

Figure 12:
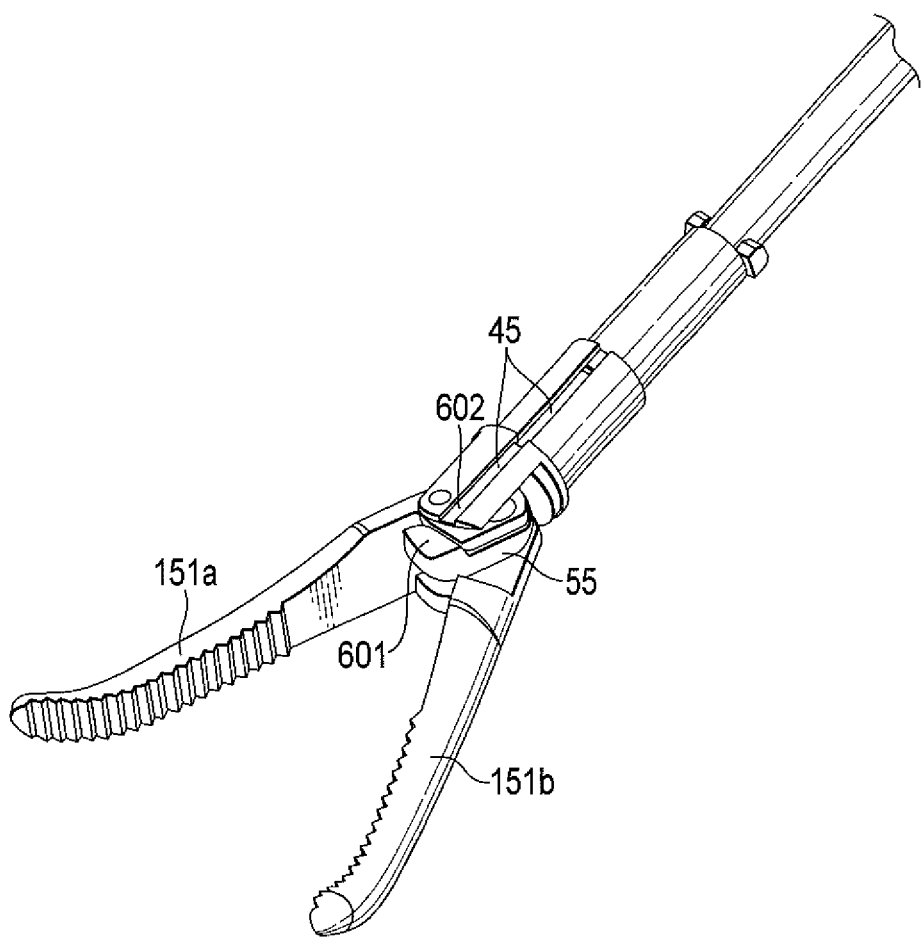
FIG. 12 is a perspective view of the vicinity of a distal end portion of a forceps unit only with a groove and without a through hole portion.
Figure 13:
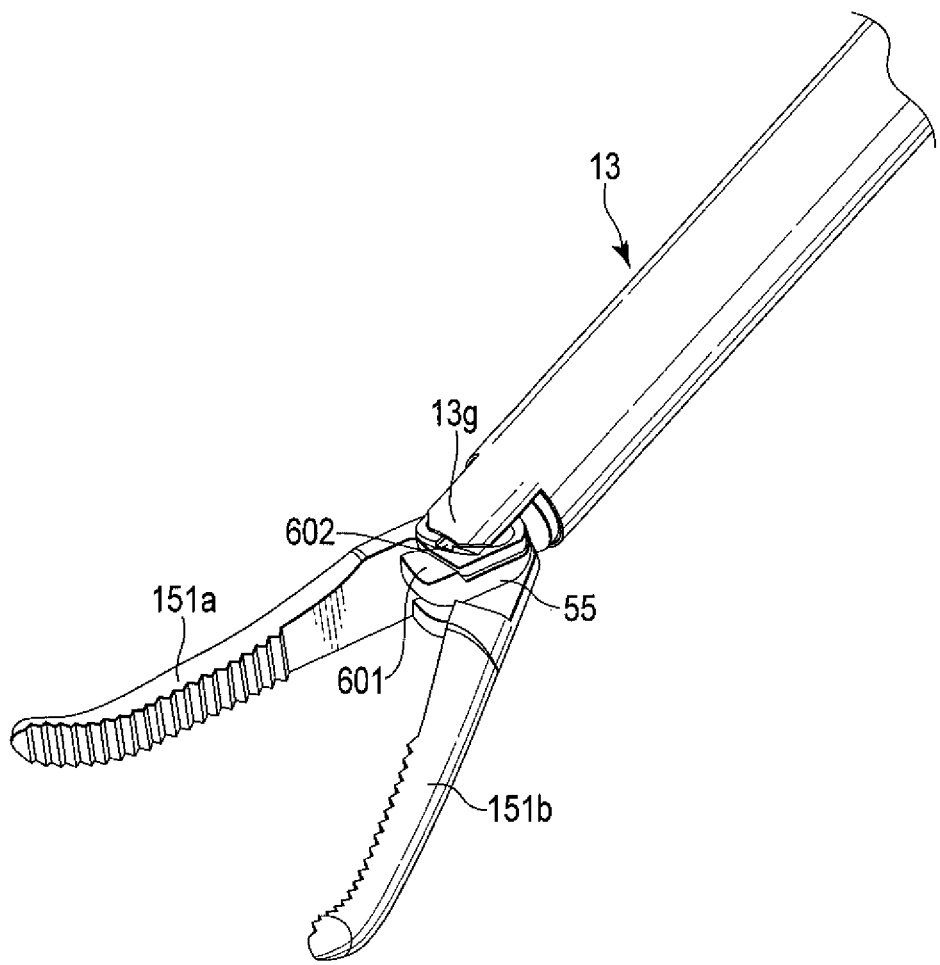
FIG. 13 is a perspective view of the vicinity of a distal end portion of a treatment instrument only with a groove and without a through hole portion.

Referring now to FIG. 12 and FIG. 13, a third embodiment will be described. The same parts as in the foregoing first embodiment are denoted with the same reference signs and a detailed description thereof will be omitted. Some parts are omitted in the drawings for the sake of simplification.

As shown in FIG. 12 and FIG. 13, a flow channel portion 41 of a distal end cover member 12 is formed with a groove portion 45 alone. Through hole portions 47, 55d provided in the distal end cover member 12 and a forceps piece 151a and an insulating member 55, which are present in the first and second embodiments, are not present. In order not to hinder a flow of water from an opening portion 602 disposed in the groove portion 45 of the distal end cover member 12, the insulating member 55 has a flat portion 601 disposed at the distal end portion of the insulating member 55.

In normal laparoscopic surgery, the forceps pieces 151a, 151b are always located below the proximal end portion of a shaft member 13. For this reason, liquid can be supplied near the forceps pieces 151a, 151b with the groove portion 45 alone. A groove cover member 13g can be eliminated as long as the angle of the shaft member 13 relative to the horizontal surface is inclined at about 30 degrees or more.

Accordingly, the present embodiment can provide a low-cost bipolar electrical treatment instrument for use in a body cavity, which can coagulate an affected area by high frequency power while supplying liquid to the affected area.

[First Modification]

Figure 14:
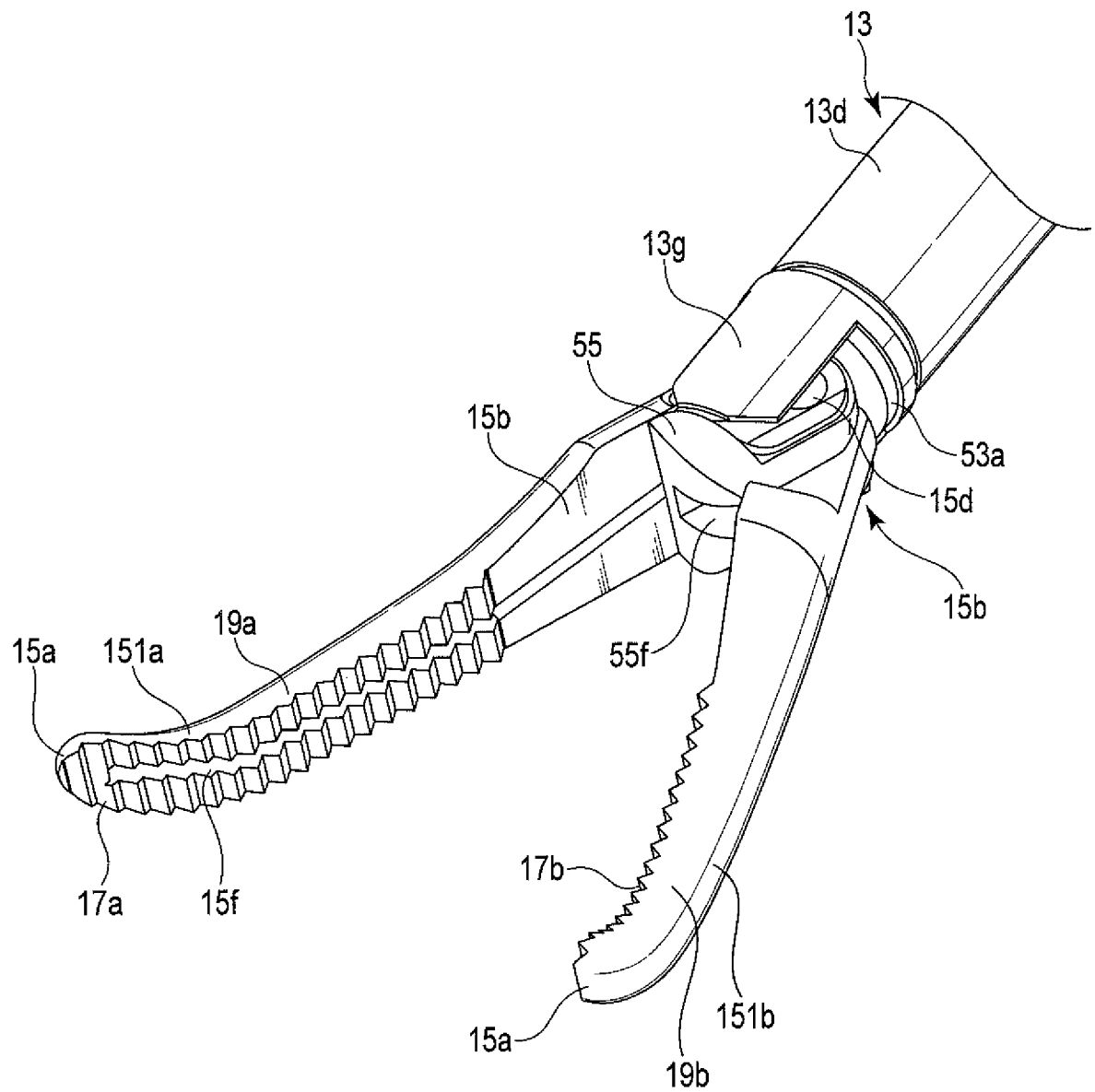
FIG. 14 is a perspective view of the vicinity of a distal end portion of a shaft member with a grip groove portion disposed at a grip surface according to a first modification.
Figure 15:
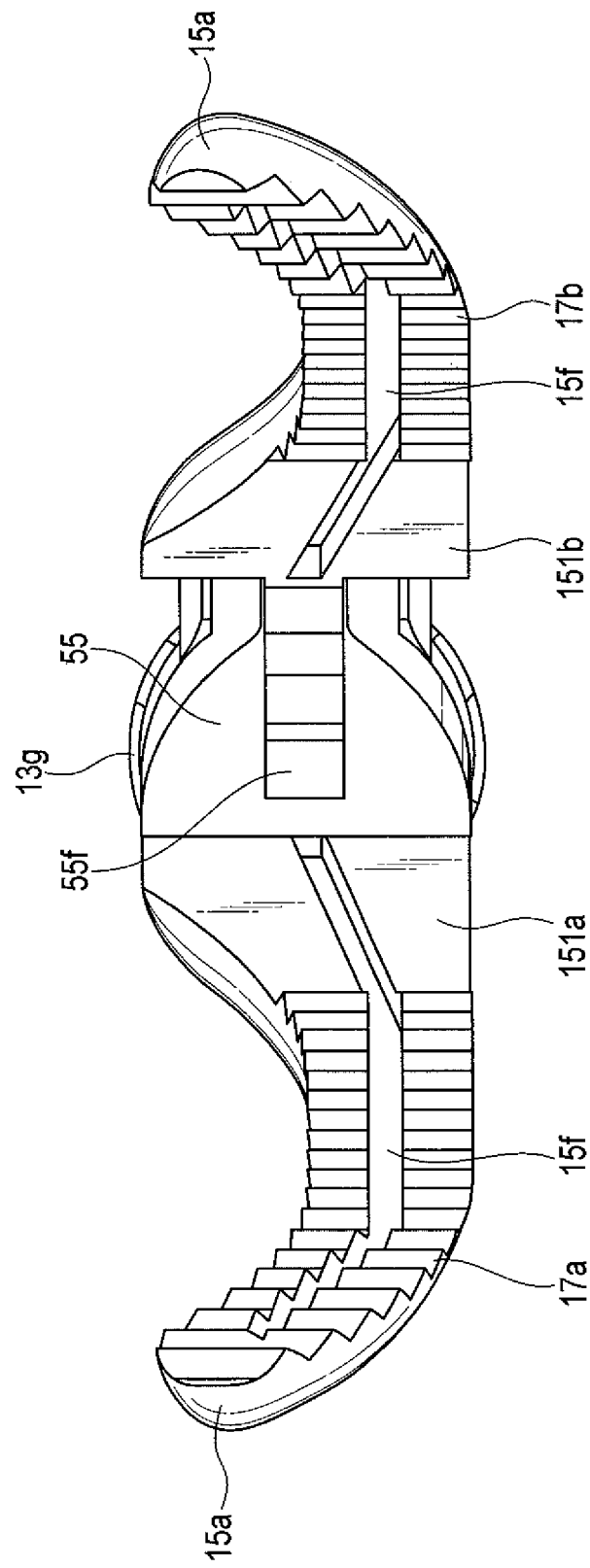
FIG. 15 is a front view of forceps pieces shown in FIG. 14.

A first modification to the foregoing embodiments will be described with reference to FIG. 14 and FIG. 15. At least one of a grip surface 17a of one forceps piece 151a and a grip surface 17b of the other forceps piece 151b may have a grip groove portion 15f that communicates with an opening portion 55f and is disposed along the longitudinal direction of the forceps pieces 151a, 151b to allow a fluid to flow from a proximal end portion 15b to a distal end portion 15a of the forceps pieces 151a, 151b.

Accordingly, in the present modification, the liquid can be fed to the distal end portion 15a of the forceps pieces 151a, 151b thereby preventing adhesion of living tissue in the affected area to the grip surfaces 17a, 17b.

Provision of a plurality of grip groove portions 15f can achieve the same advantageous effects.

[Second Modification]

A second modification to the foregoing embodiments will be described with reference to FIG. 16. As shown in FIG. 16, a pair of forceps pieces 151a, 151b have insulating grip members 153a, 153b having grip surfaces 17a, 17b. The insulating grip members 153a, 153b are disposed along the longitudinal direction of the forceps pieces 151a, 151b. The insulating grip members 153a, 153b insulate high-frequency current from the liquid flowing from an opening portion 55f to the grip surfaces 17a, 17b. The insulating grip members 153a, 153b are formed of an insulating material, for example, such as a ceramic and a resin. The ceramic includes, for example, alumina and zirconia having a dielectric constant of 10 or less. The resin includes, for example, polyetheretherketone having a dielectric constant of around 2.

For example, in a case where the liquid is physiological saline solution, if the impedance of a high-frequency region relative to physiological saline solution becomes lower than the desired value, in general, the output of high-frequency power decreases, and the resulting treatment time is likely to increase. It is therefore necessary to prevent a reduction in impedance.

The prevention of reduction in impedance will be described below. It is noted that the forceps pieces 151a, 151b shown in FIG. 17A and FIG. 17B do not have the insulating grip members 153a, 153b.

Let the opening angle be θ1 in a case where the opening angle between the forceps pieces 151a and 151b is large as shown in FIG. 17A, for example, in a state in which the forceps pieces 151a and 151b are opened to the maximum.

Let the opening angle be θ2 in a case where the opening angle between the forceps pieces 151a and 151b is small as shown in FIG. 17B, for example, in a state in which the grip surfaces of the forceps pieces 151a, 151b are entirely wet with liquid 150. The relationship between θ1 and θ2 is θ1>θ2.

As shown in FIG. 17A and FIG. 17B, when the opening angle is θ1, the wet area of the forceps pieces 151a, 151b wet with the liquid 150 is smaller than when the opening angle is θ2.

As described above, the wet area of the forceps pieces 151a, 151b is affected by the opening angle between the forceps pieces 151a and 151b. The wet area increases as the opening angle decreases. The liquid 150 such as physiological saline solution has a high electrical conductivity in a high-frequency region. This means that, in general, the wet area increases as the impedance decreases. That is, the treatment time may vary with the wet area (the opening angle) of the forceps pieces 151a, 151b.

In the present modification, therefore, the forceps pieces 151a, 151b have the insulating grip members 153a, 153b as shown in FIG. 17C and FIG. 17D. The insulating grip members 153a, 153h prevent reduction in impedance even when the opening angle is small.

The length of the insulating grip members 153a, 153b will be described briefly below.

As shown in FIG. 17C, let the length of the forceps piece 151a be L. The length of the forceps piece 151a represents a position from the distal end portion of the forceps piece 151a to an action pin member 15d.

As shown in FIG. 17C, let the maximum opening angle between the forceps pieces 151a and 151b be θ1.

As shown in FIG. 17D, let the opening angle between the forceps pieces 151a and 151b be θ2 in a state in which the grip surface 17a including the insulating grip members 153a, 153b is entirely wet with the liquid 150.

As shown in FIG. 17C and FIG. 17D, the insulating grip members 153a, 153b are disposed from the distal end portions of the forceps pieces 151a, 151b to the desired position in the forceps pieces 151a, 151b. The desired position represents the proximal end portion side of the forceps pieces 151a, 151b (the side closer to the action pin member 15d that functions as the opening/closing shaft). The desired position represents, for example, a position in contact with the liquid 150 when the forceps pieces 151a, 151b are opened to the maximum.

As shown in FIG. 17C, let the length of the insulating grip members 153a, 153b (the length from the distal end portions of the forceps pieces 151a, 151b to the desired position) be L1. The length L1 of the insulating grip members 153a, 153b represents a position where the insulating grip members 153a, 153h can come into contact with the liquid 150 when the opening angle is θ1.

The length L1 of the insulating grip members 153a, 153b therefore is at least a length equal to or greater than $L \times (1-(\sin \theta 1/\sin \theta 2)^{1/2})$. In the present modification, L1=9.3 mm or more when L=16 mm, θ1=45°, and θ2=5°.

In more detail, a part in the forceps pieces 151a, 151b that is always wet with the liquid 150 without being affected by the opening angle is a wet part 154. The wet part 154 represents, for example, the forceps pieces 151a, 151b between the insulating grip members 153a, 153b and the action pin member 15d. The wet area of the wet part 154 is substantially constant without being affected by the opening angle between the forceps pieces 151a and 151b. In other words, because of the provision of the insulating grip members 153a, 153b, the area of the wet part 154 of the forceps pieces 151a, 151b does not vary even when the opening angle between the forceps pieces 151a and 151b changes. The provision of the insulating grip members 153a, 153b having such a length can prevent reduction in impedance.

As described above, in the present modification, the provision of the insulating grip members 153a, 153b allows the wet area to be substantially constant and prevents reduction in impedance even when the opening angle is small. Accordingly, the present modification can prevent reduction in output of high-frequency power and prevent increase in treatment time. That is, the present modification can reliably prevent the treatment time from varying in accordance with the opening angle (the wet area) between the forceps pieces 151a and 151b.

In the present modification, the insulating grip members 153a, 153b are disposed from the distal end portions of the forceps pieces 151a, 151b to the desired position in the forceps pieces 151a, 151b, thereby reliably preventing reduction in output of high-frequency power and preventing increase in the treatment time.

The insulating grip members 153a, 153b may be removable from the forceps pieces 151a, 151b as shown in FIG. 18. In this case, for example, the insulating grip members 153a, 153b each have a protrusion 155a, and the forceps pieces 151a, 151b each have a recession 155b in which the protrusion 155a removably slides. Accordingly, in the present modification, the insulating grip members 153a, 153b can be used, or the forceps pieces 151a, 151b can be directly used by removing the insulating grip members 153a, 153b.

In the present modification, metal members having the same shape as the insulating grip members 153a, 153b and having the grip surfaces 17a, 17b and the protrusion 155a may be disposed at the forceps pieces 151a, 151b with the recession 155b interposed.

[Third Modification]

A third modification to the forgoing embodiments will be described with reference to FIG. 19.

At least one of a forceps piece 151a and the other forceps piece 151b has an open window portion 156. The open window portion 156 is disposed in the forceps piece 151a so as to pass through the forceps piece 151a including a grip surface 17a in the thickness direction of the forceps piece 151a. In this respect, the forceps piece 151b has the same structure.

In the present modification, liquid supplied from an opening portion 55f is accumulated in the open window portion 156, thereby preventing the high-frequency-heated liquid from unnecessarily flowing out of the vicinity of the forceps piece 151a and the forceps piece 151b.

The present invention is not limited to the foregoing embodiments per se and, in practice, can be embodied with components modified without departing from the spirit of the invention. A plurality of components disclosed in the forgoing embodiments can be combined as appropriate to form a variety of inventions.

What is claimed is:

1. A high-frequency electrosurgical treatment instrument for operations, comprising:
    a pair of forceps pieces each including a corresponding grip surface, the grip surfaces being opposed to each other to grip an affected area, the pair of forceps pieces being configured to open and close relative to each other;
    an insulating member disposed at a proximal end portion of each of the pair of forceps pieces, the insulating member and one of the pair of forceps pieces being pivotably coupled to another one of the pair of forceps pieces via an action pin member, the insulating member being configured to insulate the one of the pair of forceps pieces from the other one of the pair of forceps pieces;
    a transmission member coupled to the one of the pair of forceps pieces such that the one of the pair of forceps pieces and the other one of the pair of forceps pieces are pivotably coupled to each other;
    a manipulation rod including a distal end portion and a proximal end portion, the distal end portion being fixed to the transmission member;
    a distal end cover including a fulcrum that pivotably couples the one of the pair of forceps pieces to the other one of the pair of forceps pieces;
    an insulating tubular member disposed in the distal end cover, the insulating tubular member insulating an inner surface of the distal end cover;
    a shaft into which the manipulation rod is inserted to cover the manipulation rod so as to wrap the manipulation rod from the distal end portion to the proximal end portion, the shaft being inserted into a body cavity together with the manipulation rod;
    a manipulation portion including a movable handle removably coupled to the proximal end portion of the manipulation rod, and a fixed handle removably coupled to a proximal end of the shaft;
    a flow channel having a ring shape, the flow channel being formed in a space between the manipulation rod and the shaft in a radial direction of the shaft, the flow channel being disposed along a longitudinal direction of the manipulation rod, when the manipulation rod is inserted into the shaft, to allow liquid to flow through the flow channel;
    a groove configured to communicate with the flow channel, the groove being disposed along the longitudinal direction of the manipulation rod on an outer peripheral surface of the distal end cover, the groove being configured to allow the liquid to flow from the flow channel;
    a groove cover disposed in the shaft, the groove cover covering the groove when the manipulation rod is inserted into the shaft; and
    an opening configured to communicate with the groove, the opening being disposed in the insulating member and disposed between the proximal end portions of the respective grip surfaces, and the opening opens in the longitudinal direction of the manipulation rod so that the opening is configured to supply the liquid near the respective proximal end portions of each of the pair of forceps pieces.

2. The high-frequency electrosurgical treatment instrument for operations according to claim 1, further comprising:
    a first through hole configured to communicate with the groove, the first through hole being disposed at the proximal end portion of the one of the pair of forceps pieces so as to pass through the proximal end portion of the one of the pair of forceps pieces to allow the liquid to flow from the groove; and
    a second through hole configured to communicate with the first through hole, the second through hole being disposed in the insulating member to: (i) allow the liquid to flow in from the first through hole, and (ii) supply the liquid to an extension of a central axis of the manipulation rod, wherein:
        the first through hole and the second through hole are laterally disposed on the extension of the central axis of the manipulation rod, and the first through hole and the second through hole extend from the outer peripheral surface of the distal end cover toward the central axis of the manipulation rod; and the opening is configured to communicate with the second through hole, the opening being disposed in the insulating member and on the extension of the central axis of the manipulation rod along a longitudinal direction of the insulating member to allow the liquid to flow from the second through hole.

3. The high-frequency electrosurgical treatment instrument for operations according to claim 2, wherein the first through hole and the second through hole are shaped like a long hole.

4. The high-frequency electrosurgical treatment instrument for operations according to claim 1, wherein the distal end cover has a bifurcated distal end portion, and the groove is disposed at each end of the bifurcated distal end portion of the distal end cover.

5. The high-frequency electrosurgical treatment instrument for operations according to claim 1, wherein the pair of forceps pieces are a pair of bipolar electrodes.

6. The high-frequency electrosurgical treatment instrument for operations according to claim 1, wherein the shaft includes an inlet port through which the liquid is externally fed to the flow channel.

7. The high-frequency electrosurgical treatment instrument for operations according to claim 1, wherein the liquid includes an isotonic solution.

8. The high-frequency electrosurgical treatment instrument for operations according to claim 1, wherein at least one of the grip surface of the one of the pair of forceps pieces and the grip surface of the other one of the pair of forceps pieces includes a grip groove disposed along a longitudinal direction of the corresponding one of the pair of forceps pieces.

9. The high-frequency electrosurgical treatment instrument for operations according to claim 1, wherein the pair of forceps pieces respectively include a pair of insulating grip members including the grip surfaces.

10. The high-frequency electrosurgical treatment instrument for operations according to claim 9, wherein the insulating grip members are disposed from distal end portions of the pair of forceps pieces to a position in contact with the liquid when the pair of forceps pieces are opened to their maximum.

11. The high-frequency electrosurgical treatment instrument for operations according to claim 9, wherein when the pair of forceps pieces have a length L, the pair of forceps have a maximum opening angle $\theta_1$, and the pair of forceps pieces have an opening angle $\theta_2$ in a state in which the grip surfaces of the insulating grip members are entirely wet with the liquid, a length L1 of the insulating grip members from the distal end portions of the pair of forceps pieces is at least equal to or greater than $L \times (1-(\sin\theta_1/\sin\theta_2)^{1/2})$.

12. The high-frequency electrosurgical treatment instrument for operations according to claim 9, wherein:

the insulating grip members cover the respective forceps pieces for a predetermined length from a distal end portion, the insulating grip members not covering the proximal end portions of the respective forceps pieces; and the forceps pieces are configured to bring proximal end portions of the insulating grip members in contact with the liquid supplied from the opening, by opening relative to each other at a maximum opening angle.

13. The high-frequency electrosurgical treatment instrument for operations according to claim 1, wherein at least one of the pair of forceps pieces has an open window.

14. The high-frequency electrosurgical treatment instrument for operations according to claim 1, wherein the manipulation rod includes a sheath that surrounds and insulates the manipulation rod.

15. The high-frequency electrosurgical treatment instrument for operations according to claim 1, wherein the shaft includes a sheath that surrounds and insulates the shaft.

16. The high-frequency electrosurgical treatment instrument for operations according to claim 1, wherein the manipulation rod, the flow channel, and the shaft are arranged concentrically.

17. The high-frequency electrosurgical treatment instrument for operations according to claim 1, further comprising a through-hole that is inclined relative to the longitudinal direction and extends from the outer peripheral surface of the distal end cover towards a central axis of the manipulation rod, wherein a proximal end of the through-hole is in communication with the groove and a distal end of the through-hole is in communication with the opening.

18. The high-frequency electrosurgical treatment instrument for operations according to claim 1, wherein:

the groove is formed on the outer peripheral surface of the distal end cover, the groove is configured to communicate with the flow channel at a first end, and the groove is configured to allow the liquid to flow from the flow channel to the respective proximal end portions of each of the pair of forceps pieces at a second end of the groove.

19. A high-frequency electrosurgical system for operations, comprising:

a pair of forceps pieces each including a corresponding grip surface, the grip surfaces being opposed to each other to grip an affected area, the pair of forceps pieces being configured to open and close relative to each other;

an insulating member disposed at a proximal end portion of each of the pair of forceps pieces, the insulating member and one of the pair of forceps pieces being pivotably coupled to another one of the pair of forceps pieces via an action pin member, the insulating member being configured to insulate the one of the pair of forceps pieces from the other one of the pair of forceps pieces;

a transmission member coupled to the one of the pair of forceps pieces such that the one of the pair of forceps pieces and the other one of the pair of forceps pieces are pivotably coupled to each other;

a manipulation rod including a distal end portion and a proximal end portion, the distal end portion being fixed to the transmission member;

a distal end cover including a fulcrum that pivotably couples with the one of the pair of forceps pieces to the other one of the pair of forceps pieces;

an insulating tubular member disposed in the distal end cover, the insulating tubular member insulating an inner surface of the distal end cover;

a shaft into which the manipulation rod is inserted to cover the manipulation rod so as to wrap the manipulation rod from the distal end portion to the proximal end portion, the shaft being inserted into a body cavity together with the manipulation rod;

a manipulation portion including a movable handle removably coupled to the proximal end portion of the manipulation rod, and a fixed handle removably coupled to a proximal end portion of the shaft;

a flow channel having a ring shape, the flow channel being formed in a space between the manipulation rod and the shaft in a radial direction of the shaft, the flow channel being disposed along a longitudinal direction of the manipulation rod, when the manipulation rod member is inserted into the shaft member, to allow liquid to flow through the flow channel;

a groove configured to communicate with the flow channel, the groove being disposed along the longitudinal direction of the manipulation rod on an outer peripheral surface of the distal end cover, the groove being configured to allow the liquid to flow from the flow channel;

a groove cover disposed in the shaft, the groove cover covering the groove when the manipulation rod is inserted into the shaft;

an opening configured to communicate with the groove, the opening being disposed in the insulating member and disposed between the proximal end portions of the respective grip surfaces, and the opening opens in the longitudinal direction of the manipulation rod so that the opening is configured to supply the liquid near the respective proximal end portions of each of the pair of forceps pieces;

a connector including a return electrode that electrically conducts with the one of the pair of forceps pieces, and an active electrode that electrically conducts with the other one of the pair of forceps pieces;

a liquid storage configured to convey the liquid to the flow channel; and a power supply electrically connected with the connector to supply power to the pair of forceps pieces.

20. The high-frequency electrosurgical system for operations according to claim 19, wherein the manipulation rod, the flow channel, and the shaft are arranged concentrically.

21. The high-frequency electrosurgical system for operations according to claim 19, further comprising a through-hole that is inclined relative to the longitudinal direction and extends from the outer peripheral surface of the distal end cover towards a central axis of the manipulation rod, wherein a proximal end of the through-hole is in communication with the groove and a distal end of the through-hole is in communication with the opening.

22. A high-frequency electrosurgical treatment instrument, comprising:

a pair of forceps pieces each including a corresponding grip surface, the grip surfaces being opposed to each other to grip an affected area, the pair of forceps pieces being configured to open and close relative to each other to hold the affected area between the pair of forceps pieces so that a high-frequency current is applied to the held affected area;

an insulating member disposed at a proximal end portion of each of the pair of forceps pieces, the insulating member being configured to insulate one of the pair of forceps pieces from another one of the pair of forceps pieces;

a manipulation rod;

a shaft configured to cover the manipulation rod from a distal end portion to a proximal end portion of the manipulation rod;

a flow channel extending along a longitudinal direction of the manipulation rod and extending between the manipulation rod and the shaft, the flow channel allowing a liquid supplied from a liquid supply source to flow through the flow channel; and an opening communicating with the flow channel and disposed in the insulating member, the opening being located between the proximal end portions of the respective grip surfaces, the opening opens in the longitudinal direction of the manipulation rod, the opening being configured to supply the liquid to an area where the affected area is held between the proximal end portions of the pair of forceps pieces.

* * * * *